US006927237B2

(12) United States Patent
Hei et al.

(10) Patent No.: US 6,927,237 B2
(45) Date of Patent: Aug. 9, 2005

(54) TWO SOLVENT ANTIMICROBIAL COMPOSITIONS AND METHODS EMPLOYING THEM

(75) Inventors: Robert D. P. Hei, Baldwin, WI (US); Brandon Herdt, Hastings, MN (US); Lawrence Grab, Woodbury, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 10/086,765

(22) Filed: Feb. 28, 2002

(65) Prior Publication Data

US 2002/0168422 A1 Nov. 14, 2002

Related U.S. Application Data

(63) Continuation-in-part of application No. 09/560,170, filed on Apr. 28, 2000, and a continuation-in-part of application No. 09/641,775, filed on Aug. 18, 2000, now Pat. No. 6,544,942, and a continuation-in-part of application No. 09/794,790, filed on Feb. 27, 2001, now Pat. No. 6,593,283.

(51) Int. Cl.[7] ........................ A01N 37/00; A01N 29/00; A01N 59/00; A61K 31/19; A61K 31/02

(52) U.S. Cl. ....................... 514/557; 514/558; 514/574; 514/743; 424/661; 424/723

(58) Field of Search ................................ 514/557, 558, 514/743, 547; 424/661, 723

(56) References Cited

U.S. PATENT DOCUMENTS

| | | | |
|---|---|---|---|
| 2,512,640 | A | 6/1950 | Greenspan et al. |
| 3,122,417 | A | 2/1964 | Blasor et al. |
| 3,248,281 | A | 4/1966 | Goodenough |
| 3,350,265 | A | 10/1967 | Rubinstein et al. |
| 3,514,278 | A | 5/1970 | Brink |
| 3,895,116 | A | 7/1975 | Herting et al. |
| 3,996,386 | A | 12/1976 | Malkki et al. |
| 4,041,149 | A | 8/1977 | Gaffar et al. |
| 4,051,058 | A | 9/1977 | Böwing et al. |
| 4,051,059 | A | 9/1977 | Böwing et al. |
| 4,129,517 | A | 12/1978 | Eggensperger et al. |
| 4,191,660 | A | 3/1980 | Schreiber et al. |
| 4,244,884 | A | 1/1981 | Hutchins et al. |
| 4,370,199 | A | 1/1983 | Orndorff |
| 4,404,040 | A | 9/1983 | Wang |
| 4,477,438 | A | 10/1984 | Willcockson et al. |
| 4,478,683 | A | 10/1984 | Orndorff |
| 4,501,681 | A | 2/1985 | Groult et al. |
| 4,529,534 | A | 7/1985 | Richardson |
| 4,557,898 | A | 12/1985 | Greene et al. |
| 4,592,488 | A | 6/1986 | Simon et al. |
| 4,613,452 | A | 9/1986 | Sanderson |
| 4,655,781 | A | 4/1987 | Hsieh et al. |
| 4,666,622 | A | 5/1987 | Martin et al. |
| 4,715,980 | A | 12/1987 | Lopes et al. |
| 4,738,840 | A | 4/1988 | Simon et al. |
| 4,802,994 | A | 2/1989 | Mouche et al. |
| 4,865,752 | A | 9/1989 | Jacobs |

(Continued)

FOREIGN PATENT DOCUMENTS

| | | | | |
|---|---|---|---|---|
| CA | 2181416 | | | 1/1997 |
| DE | 35 43 500 | A1 | | 6/1987 |
| DE | 39 06 044 | A1 | | 8/1990 |
| DE | 197 51 391 | A1 | | 7/1998 |
| EP | 0 195 619 | A2 | | 9/1986 |
| EP | 0 233 731 | A2 | | 8/1987 |
| EP | 0 404 293 | A2 | | 12/1990 |
| EP | 0 461 700 | A1 | | 12/1991 |
| EP | 0 569 066 | A1 | | 11/1993 |
| EP | 0 667 392 | A2 | | 2/1995 |
| EP | 0 779 357 | A1 | | 12/1995 |
| EP | 0 805 198 | A1 | | 7/1996 |
| EP | 0 843 001 | A1 | | 11/1996 |
| EP | 0 985 342 | A2 | | 3/2000 |
| FR | 2 231 301 | A | | 3/1977 |
| FR | 2 324 626 | A | | 4/1977 |
| GB | 1 494 109 | | | 12/1977 |
| GB | 2 255 507 | | | 11/1992 |
| JP | 63057502 | | | 3/1988 |
| JP | 05085901 | | | 4/1993 |
| JP | 06219911 | | * | 8/1994 |
| JP | 09194419 | | | 7/1997 |
| JP | 10130173 | | | 5/1998 |
| LU | 78 568 | A | | 4/1978 |
| RU | 2102447 | C1 | | 8/1996 |
| WO | WO 93/01716 | | | 2/1993 |
| WO | WO 94/21122 | | | 9/1994 |
| WO | WO 94/23575 | | | 10/1994 |
| WO | WO 95/34537 | | | 12/1995 |
| WO | WO 96/30474 | | | 10/1996 |
| WO | WO 98/28267 | | | 7/1998 |
| WO | WO 99/51095 | | | 10/1999 |
| WO | WO-0004777 | | * | 2/2000 |

OTHER PUBLICATIONS

Furuta, T. et al., "Relationship between the Effects on Bactericidal Actvity of Selected Disinfectants and the Hydrophobic Characters of Dibasic Acid Diesters", *Chem. Pharm. Bull.*, 40(5):1309–1312 (1992).

Copy of International Search Report, dated Oct. 10, 2002 (7 Pages).

Bell, K. et al., "Reduction of foodborne micro–organisms on beef carcass tissue using acetic acid, sodium bicarbonate, and hydrogen peroxide spray washes", *Food Microbiology*, vol. 14, pp. 439–448 (1997).

(Continued)

*Primary Examiner*—Alton Pryor
(74) *Attorney, Agent, or Firm*—Merchant & Gould P.C.

(57) ABSTRACT

The present invention relates to two solvent antimicrobial compositions and methods employing these two solvent compositions. The two solvent compositions typically contain a second solvent that is not or is only sparingly soluble in a diluting solvent. The two solvent composition can form a clear single-phase solution. The two solvent antimicrobial compositions can reduce the population of microbes on various surfaces such as facilities, containers, or equipment found in food, beverage, or pharmaceutical industries at temperatures between about −70° C. to about 100° C.

34 Claims, 1 Drawing Sheet

U.S. PATENT DOCUMENTS

| | | | |
|---|---|---|---|
| 4,900,721 | A | 2/1990 | Bansemir et al. |
| 4,906,617 | A | 3/1990 | Jacquet et al. |
| 4,908,306 | A | 3/1990 | Lorincz |
| 4,917,815 | A | 4/1990 | Beilfuss et al. |
| 4,923,077 | A | 5/1990 | Van Iperen et al. |
| 4,937,066 | A | 6/1990 | Vlock |
| 4,943,414 | A | 7/1990 | Jacobs et al. |
| 4,945,110 | A | 7/1990 | Brokken et al. |
| 4,996,062 | A | 2/1991 | Lehtonen et al. |
| 4,997,025 | A | 3/1991 | Post et al. |
| 4,997,571 | A | 3/1991 | Roensch et al. |
| 5,004,760 | A | 4/1991 | Patton et al. |
| 5,010,109 | A | 4/1991 | Inoi |
| 5,015,408 | A | 5/1991 | Reuss |
| 5,043,176 | A | 8/1991 | Bycroft et al. |
| 5,069,286 | A | 12/1991 | Roensch et al. |
| 5,078,896 | A | 1/1992 | Rorig et al. |
| 5,084,239 | A | 1/1992 | Moulton et al. |
| 5,093,140 | A | 3/1992 | Watanabe |
| 5,114,178 | A | 5/1992 | Baxter |
| 5,114,718 | A | 5/1992 | Damani |
| 5,122,538 | A | 6/1992 | Lokkesmoe et al. |
| 5,129,824 | A | 7/1992 | Keller |
| 5,130,124 | A | 7/1992 | Merianos et al. |
| 5,139,788 | A | 8/1992 | Schmidt |
| 5,176,899 | A | 1/1993 | Montgomery |
| 5,200,189 | A | 4/1993 | Oakes et al. |
| 5,208,057 | A | 5/1993 | Greenley et al. |
| 5,234,703 | A | 8/1993 | Guthery |
| 5,234,719 | A | 8/1993 | Richter et al. |
| 5,268,003 | A | 12/1993 | Coope et al. |
| 5,292,447 | A | 3/1994 | Venturello et al. |
| 5,314,687 | A | 5/1994 | Oakes et al. |
| 5,336,500 | A | 8/1994 | Richter et al. |
| 5,364,650 | A | 11/1994 | Guthery |
| 5,391,324 | A | 2/1995 | Reinhardt et al. |
| 5,409,713 | A | 4/1995 | Lokkesmoe et al. |
| 5,419,908 | A | 5/1995 | Richter et al. |
| 5,435,808 | A | 7/1995 | Holzhauer et al. |
| 5,436,008 | A | 7/1995 | Richter et al. |
| 5,437,868 | A | 8/1995 | Oakes et al. |
| 5,489,434 | A | 2/1996 | Oakes et al. |
| 5,494,588 | A | 2/1996 | LaZonby |
| 5,508,046 | A | 4/1996 | Cosentino et al. |
| 5,512,309 | A | 4/1996 | Bender et al. |
| 5,578,134 | A | 11/1996 | Lentsch et al. |
| 5,591,706 | A | 1/1997 | Ploumen |
| 5,595,967 | A | 1/1997 | Miracle et al. |
| 5,597,790 | A | 1/1997 | Thoen |
| 5,616,335 | A | 4/1997 | Nicolle et al. |
| 5,616,616 | A | 4/1997 | Hall, II et al. |
| 5,632,676 | A | 5/1997 | Kurschner et al. |
| 5,641,530 | A | 6/1997 | Chen |
| 5,656,302 | A | 8/1997 | Cosentino et al. |
| 5,658,467 | A | 8/1997 | LaZonby et al. |
| 5,674,538 | A | 10/1997 | Lokkesmoe et al. |
| 5,674,828 | A | 10/1997 | Knowlton et al. |
| 5,683,724 | A | 11/1997 | Hei et al. |
| 5,712,239 | A | 1/1998 | Knowlton et al. |
| 5,718,910 | A | 2/1998 | Oakes et al. |
| 5,756,139 | A | 5/1998 | Harvey et al. |
| 5,785,867 | A | 7/1998 | LaZonby et al. |
| 5,840,343 | A | 11/1998 | Hall, II et al. |
| 5,851,483 | A | 12/1998 | Nicolle et al. |
| 5,891,392 | A | 4/1999 | Monticello et al. |
| 5,900,256 | A | 5/1999 | Scoville, Jr. et al. |
| 5,902,619 | A | 5/1999 | Rubow et al. |
| 5,968,539 | A | 10/1999 | Beerse et al. |
| 5,989,611 | A | 11/1999 | Stemmler, Jr. et al. |
| 5,998,358 | A | 12/1999 | Herdt et al. |
| 6,010,729 | A | 1/2000 | Gutzmann et al. |
| 6,024,986 | A | 2/2000 | Hei |
| 6,033,705 | A | 3/2000 | Isaacs |
| 6,049,002 | A | 4/2000 | Mattila et al. |
| 6,096,226 | A | 8/2000 | Fuchs et al. |
| 6,096,266 | A | 8/2000 | Duroselle |
| 6,096,348 | A | 8/2000 | Miner et al. |

OTHER PUBLICATIONS

Eggensperger, H., "Disinfectants Based on Peracid–Splitting Compounds", *Zbl. Bakt. Hyg.,* I Abt. Orig. B 168, pp. 517–524 (1979).

Lion C. et al., "New decontaminants. Reaction of peroxyacid esters with toxic insecticides", *Bull. Soc. Chim. Belg.,* vol. 100, No. 7, pp. 555–559 (1991).

Merka, V. et al., "Disinfectant properties of some peroxide compounds.", Abstract No. 67542e, *Chemical Abstracts,* vol. 67 (1967).

Mulder, R.W.A.W. et al., "Research Note: Salmonella Decontamination of Broiler Carcasses with Lactic Acid, L–Cysteine, and Hydrogen Peroxide", *Poultry Science,* vol. 66, pp. 1555–1557 (1987).

Parker, W. et al., "Peroxides. II. Preparation, Characterization and Polarographic Behavior of Longchiang Aliphatic Peracids", *Synthesis and Properties of LongChain Aliphatic Peracids,* vol. 77, pp. 4037–4041 (Aug. 5. 1955).

Parker, W. et al., "Peroxides. IV. Aliphatic Diperacids", *Aliphatic Diperacids,* vol. 79, pp. 1929–1931 (Apr. 20, 1957).

Towle, G. et al., "Industrial Gums polysaccharides and Their Derivatives", Second Edition, Ch. XIX, "Pectin", pp. 429–444 (year unknown).

Armak Chemicals, "NEO–FAT Fatty Acids", *Alco Chemicals Inc.,* Bulletin No. 86–17 (1986).

Computer search results — Level 1 — 5 patents (Mar. 1994).

Computer search results from Ecolab Information Center (Jun. 1998).

"Emery™ Fatty and Dibasic Acids Specifications and Characteristics", *Emery Industries,* Bulletin 145, (Oct. 1983).

Pfizer Chemical Division, "Pfizer Flocon™ Biopolymers for Industrial Uscs (xanthan broths)", Data Sheet 679, pp. 1–4 (year unknown).

"Indirect food additives: adjuvants, production aids, and sanitizers", *Fed. Regist.,* vol. 61, No. 108, pp. 28051–28053 (Jun. 4, 1996) (abstract only).

Search Result from Database WPI and Database INPADOC.

Copy of International Search Report dated Jan. 30, 2002 (10 pages).

Search Report for the use of amine oxides with hydrogen peroxide in bleaching, sanitizing, disinfectant or hard surface cleaners.

* cited by examiner

TWO SOLVENT ANTIMICROBIAL COMPOSITIONS AND METHODS EMPLOYING THEM

CROSS-REFERENCE TO RELATED APPLICATIONS

This application is a continuation-in-part of U.S. patent application Ser. No. 09/560,170, filed Apr. 28, 2000, a continuation-in-part of U.S. patent application Ser. No. 09/641,775, filed Aug. 18, 2000, now U.S. Pat. No. 6,544, 942 and a continuation-in-part of U.S. patent application Ser. No. 09/794,790, filed Feb. 27, 2001, now U.S Pat. No. 6,593,283. The disclosures of each of these applications is incorporated herein by reference.

FIELD OF THE INVENTION

The present invention relates to two solvent antimicrobial compositions and methods employing these two solvent compositions. The two solvent compositions typically contain a second solvent that is not or is only sparingly soluble in a diluting solvent. The two solvent composition can form a clear single-phase solution. The two solvent antimicrobial compositions can reduce the population of microbes on various surfaces such as facilities, containers, or equipment found in food, beverage, or pharmaceutical industries at temperatures between about −70° C. to about 100° C.

BACKGROUND OF THE INVENTION

There has been a longstanding need for antimicrobial agents having improved antimicrobial efficacy and improved speed of action. The specific requirements for such agents vary according to the intended application (e.g., sanitizer, disinfectant, sterilant, aseptic packaging treatment, etc.) and the applicable public health requirements. For example, as set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2), a sanitizer should provide a 99.999% reduction (5-log order reduction) within 30 seconds at room temperature, 25±2° C., against several test organisms.

Many antimicrobial agents (e.g., iodophors, peracids, hypochlorites, chlorine dioxide, ozone, etc.) have a broad spectrum of antimicrobial properties. However, these agents sometimes have inadequate activity against bacterial spores, fungal spores, and fungi. This is particularly true under conditions requiring use of low level of such an agent, for example, to minimize corrosion of equipment or packaging, to provide adequate rinsing of a surface, to yield negligible residual antimicrobial agent, to minimize off-gassing of the antimicrobial agent, or to minimize chemical levels in the air. Killing, inactivating, or otherwise reducing the active population of bacterial spores and fungi on surfaces is particularly difficult. Bacterial spores have a unique chemical composition of spore layers that make them more resistant than vegetative bacteria to the antimicrobial effects of chemical and physical agents. Likewise, the unique chemical composition of fungal cells, especially mold spores, makes them more resistant to chemical and physical agents than are other microorganisms. This resistance can be particularly troublesome when the spores or fungi are located on surfaces such as food, food contact sites, ware, hospitals and veterinary facilities, surgical implements, and hospital and surgical linens and garments.

Control of the mold *Chaetomium funicola*, and of bacterial spore-forming microorganisms of the *Bacillus* species, can be especially important during food packaging, particularly during cold or hot aseptic filling of food and beverage products. Microorganisms of the *Bacillus* species include *Bacillus cereus, Bacillus mycoides, Bacillus subtilis, Bacillus anthracis*, and *Bacillus thuringiensis*. These latter microorganisms share many phenotypic properties, have a high level of chromosomal sequence similarity, and are known enterotoxin producers. *Bacillus cereus* is one of the most problematic because *Bacillus cereus* has been identified as possessing increased resistance to germicidal chemicals used to decontaminate environmental surfaces. For example, Blakistone et al., *Efficacy of Oxonia Active Against Selected Sporeformers*, Journal of Food Protection, Volume 62, pp.262–267, reported that *Bacillus cereus* was more tolerant of the effects of conventionally formulated peroxyacetic acid germicides than all other spore-forming bacteria tested, including other *Bacillus* and *Clostridium* species.

*Bacillus cereus* is frequently diagnosed as a cause of gastrointestinal disorders and has been suggested to be the cause of several food-borne illness outbreaks. Due to its rapid sporulating capacity, *Bacillus cereus* easily survives in the environment. *Bacillus cereus* is omnipresent in nature, and consequently can usually be found in animal feed and fodder. *Bacillus cereus* can contaminate raw milk via feces and soil, and can survive intestinal passage in cows and the pasteurization process.

*Bacillus cereus* is also known to cause serious human illness via environmental contamination. For example, *Bacillus cereus* is known to cause post-traumatic injury eye infections, which can result in visual impairment or loss of vision within 12–48 hours after infection. In addition, *Bacillus cereus* is regarded as transferable from washed surgical garments to patients.

Agents having greater or faster activity against bacterial spores, fungi, and other resistant microorganisms (particularly microorganisms of the *Bacillus* species) could help meet a substantial public health need, and one that is not adequately addressed by current commonly-used antimicrobial agents.

SUMMARY OF THE INVENTION

The present invention relates to two solvent antimicrobial compositions and methods employing these two solvent compositions. The two solvent compositions typically contain a second solvent that is not or is only sparingly soluble in a diluting solvent. The two solvent composition can form a clear single-phase solution. The two solvent antimicrobial compositions can reduce the population of microbes on various surfaces such as facilities, containers, or equipment found in food, beverage, or pharmaceutical industries at temperatures between about −70° C. to about 100° C.

The present invention provides, in one aspect, a method for antimicrobial treatment including applying to microbes a two solvent antimicrobial composition. A two solvent antimicrobial composition can contain a diluting solvent (e.g., water), a second solvent, and optionally, cosolvent, surfactant, or antimicrobial agent, which composition provides greater than a 1-log order reduction in the population of bacteria or spores of *Bacillus cereus* within 10 seconds at 60° C. In a preferred aspect, the methods of the invention provide broader spectrum antimicrobial action, providing greater than a 1-log order reduction within 10 seconds at 60° C. in one or more organisms such as the mold *Chaetomium funicola*. In a more preferred aspect, the methods of the invention provide greater than a 1-log order reduction within 10 seconds at 60° C. in *Chaetomium funicola, Bacillus subtilis* and *Bacillus cereus.*

In another aspect, the invention provides a method for antimicrobial treatment, including applying to microbes a two solvent antimicrobial composition, wherein the composition further includes antimicrobial agent. In a preferred embodiment, the antimicrobial agent includes a peroxycarboxylic acid, such as peroxyacetic acid, peroxyoctanoic acid, peroxyformic acid with or without a peroxide such as hydrogen peroxide; a peroxide such as hydrogen peroxide; or a halogen containing compound such as hypochlorous acid (or its salts), chlorine dioxide, hypobromous acid (or its salts), or an interhalide such as iodine monochloride, iodine dichloride, iodine tetrachloride, bromine chloride, iodine monobromide, or iodine dibromide.

In yet another aspect, the invention provides an antimicrobial concentrate and instructions for mixing the concentrate with water, wherein the concentrate includes a second solvent, an optional cosolvent or surfactant, and an optional antimicrobial agent, the amounts of second solvent and optional antimicrobial agent being sufficiently high so that the composition will provide greater than a 1-log order reduction in the population of bacteria or spores of *Bacillus cereus* within 10 seconds at 60° C.

In a further aspect, the invention provides a two solvent antimicrobial composition including a diluting solvent, a second solvent, an antimicrobial agent, and an optional cosolvent or surfactant which composition provides greater than a 1-log order reduction in the population of bacteria or spores of *Bacillus cereus* or the mold *Chaetomium funicola* within 10 seconds at 60° C.

In yet another aspect, the invention provides an antimicrobial concentrate and instructions for mixing the concentrate with water, wherein the concentrate includes a second solvent that has a density different from that of water, an optional cosolvent or surfactant, and an antimicrobial agent, the amounts of second solvent and antimicrobial agent being sufficiently high so that the composition will provide greater than a 1-log order reduction in the population of bacteria or spores of *Bacillus cereus* or the mold *Chaetomium funicola* within 10 seconds at 60° C. In a particularly preferred embodiment, the composition includes a sufficiently high amount of antimicrobial agent and antimicrobial solvent such that the composition forms a clear single-phase solution when the concentrate is mixed with water according to the instructions, and provides greater than a 1-log order reduction in the population of bacteria or spores of *Bacillus cereus* or *Bacillus subtilis* and in the population of the mold *Chaetomium funicola* within 10 seconds at 60° C.

The method and compositions of the invention are especially useful for aseptic packaging, pharmaceutical packaging, clean-in-place (CIP) or clean-out-of-place (COP) systems, hospital disinfectants, veterinary clinic disinfectants, and as sporicides or sterilants.

DETAILED DESCRIPTION

Definitions

Figure 1:
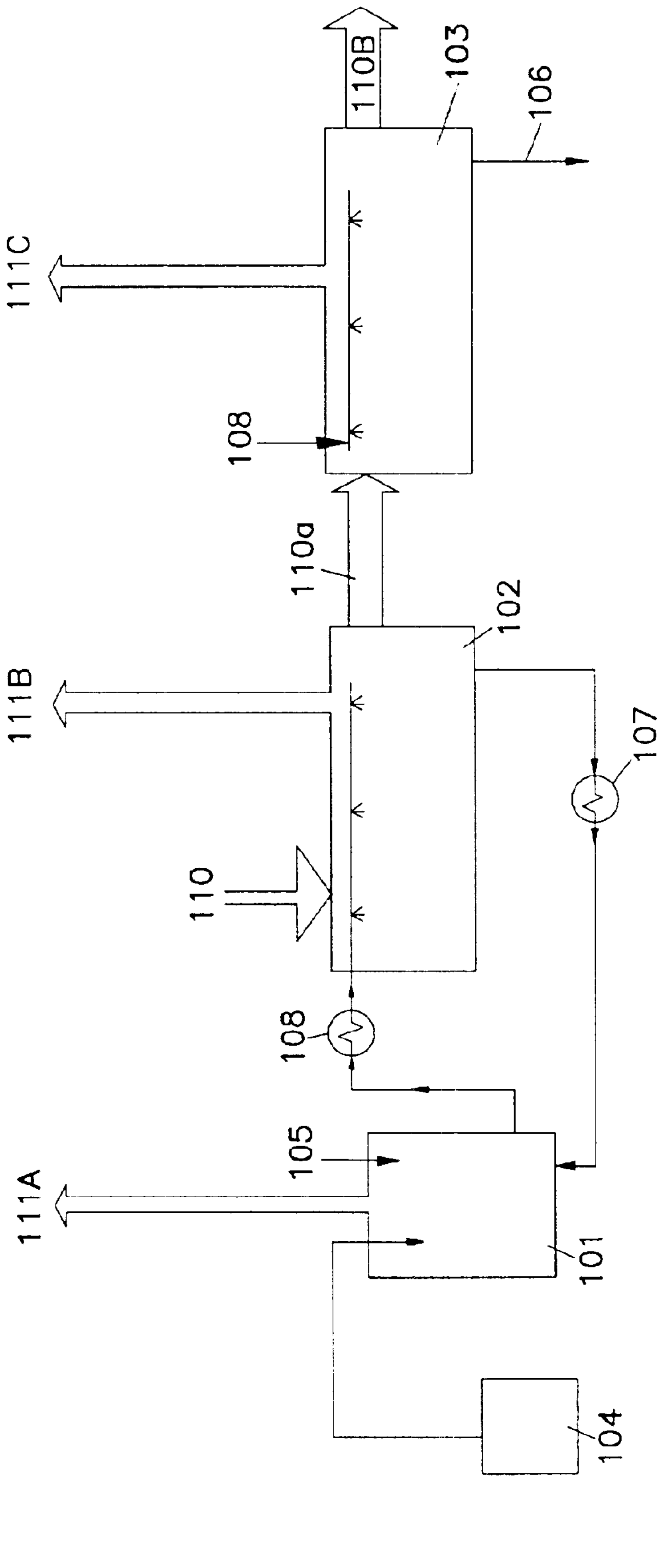
FIG. 1 is a diagram of a beverage plant, including a cold aseptic filling plant, in which either carbonated or non-carbonated beverages can be prepared and bottled.

As used herein, the phrase "antimicrobial solvent" refers to a solvent that has antimicrobial effect when applied to a microorganism alone or when mixed with a diluting solvent and, optionally, an antimicrobial agent to form a two solvent antimicrobial composition according to the present invention. For example, a sparingly soluble antimicrobial solvent may require the presence of the diluting solvent or antimicrobial agent to exhibit its antimicrobial effect. The diluting solvent can assist in making the microorganism accessible to the antimicrobial solvent. By way of further example, an antimicrobial solvent can enhance or boost the antimicrobial activity of the diluting solvent, antimicrobial agent, or the two solvent composition compared to a composition lacking the antimicrobial solvent.

As used herein, the phrase "sparingly soluble" refers to a second solvent that is soluble in a first solvent to an extent of less than about 20 wt-%, preferably less than about 10 wt-%, preferably less than about 5 wt-%, preferably less than about 3 wt-%. For example, a second solvent that is sparingly soluble in a first solvent can be soluble to an extent of 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 wt-%, to less than any of these weight percentages, to any of these weight percentages modified by about, or to less than any of these weight percentages modified by about.

As used herein, the term "microorganism" refers to any noncellular or unicellular (including colonial) organism. Microorganisms include all prokaryotes. Microorganisms include bacteria (including cyanobacteria and Mycobacteria), lichens, microfungi, protozoa, virinos, viroids, viruses, and some algae. As used herein, the term "microbe" is synonymous with microorganism.

As used herein, the term "object" refers to a something material that can be perceived by the senses, directly and/or indirectly and that might require treatment with an antimicrobial agent or composition. Objects include a surface, including a hard surface (such as glass, ceramics, metal, natural and synthetic rock, wood, and polymeric), an elastomer or plastic, woven and non-woven substrates, a food processing surface, a health care surface, a pharmaceutical surface, and the like. Objects also include a food product (and its surfaces); a body or stream of water or a gas (e.g., an air stream); and surfaces and articles employed in hospitality and industrial sectors.

As used herein, the phrase "food product" includes any food substance that might require treatment with an antimicrobial agent or composition and that is edible with or without further preparation. Food products include meat (e.g., red meat and pork), seafood, poultry, fruits and vegetables, eggs, living eggs, egg products, ready to eat food, wheat, seeds, roots, tubers, leafs, stems, corms, flowers, sprouts, seasonings, milk and milk products (e.g., yogurt, cheeses), teas, waters, or a combination thereof. The term "produce" refers to food products such as fruits and vegetables and plants or plant-derived materials that are typically sold uncooked, undercooked, or pasteurized, and, often, unpackaged, and that can sometimes be eaten raw (e.g., soy products, teas, yogurts, and juices).

As used herein, the phrase "dairy product" refers to all forms of food stuffs or beverages including or made from milk from any mammal. Dairy products include skim, reduced fat, and homogenized milk, cheese, yogurt, ice cream, frozen yogurt, sour cream, butter, and the like. Dairy products include cheese products, such as dips, spreads, snacks, and the like. Dairy products include sour cream products such as dips, spreads, and the like.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "food processing surface" refers to a surface of a tool, a package or container, a wrap or film or covering, a machine, equipment, a structure, a building, or the like that is employed as part of a food processing, preparation, or storage activity and that might require treatment with an antimicrobial agent or composition. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives. Preferred food processing surfaces include glass, multilaminate or lined cardboard cartons, mono- or multi-layer plastic bottles and cartons, aluminum containers, and the like.

As used herein, the phrase "pharmaceutical surfaces" refers to a surface of a tool, a package or container, a wrap or film or covering, a machine, equipment, a structure, a building, or the like that is employed as part of a pharmaceutical processing, preparation, or storage activity and that might require treatment with an antimicrobial agent or composition. Examples of pharmaceutical processing surfaces include surfaces of pharmaceutical processing or preparation equipment (e.g., mix vessels, tablet makers, presses, or transport equipment, including CIP lines), of pharmaceutical processing wares (e.g., utensils, mix blades, re-circulating systems, synthesis equipment), and of floors, walls, or fixtures of structures in which pharmaceutical processing occurs. Pharmaceutical processing surfaces are found and employed in the preparation of medicines, drugs, vitamin and mineral supplements, and the like. Preferred treatment pharmaceutical processing surfaces include glass, multilaminate or lined cardboard cartons, mono- or multi-layer plastic bottles and cartons, aluminum containers, foil packs, and the like.

As used herein, the phrase "air streams" includes food anti-spoilage air circulation systems and pharmaceutical circulation systems that might require treatment with an antimicrobial agent or composition. Air streams also include air streams typically encountered in hospital, surgical, infirmity, birthing, mortuary, and clinical diagnosis rooms.

As used herein, the term "waters" includes food process or transport waters and pharmaceutical process waters that might require treatment with an antimicrobial agent or composition. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity and that might require treatment with an antimicrobial agent or composition. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that might require treatment with an antimicrobial agent or composition.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g., bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

As used herein, "agricultural" or "veterinary" objects or surfaces include animal feeds, animal watering stations and enclosures, animal quarters, animal veterinarian clinics (e.g., surgical or treatment areas), animal surgical areas, and the like.

As used herein, weight percent (wt-%), percent by weight, % by weight, and the like are synonyms that refer to the concentration of a substance as the weight of that substance divided by the total weight of the composition and multiplied by 100.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "active" when applied to a peroxycarboxylic acid or another peroxy containing compound refers to the wt-% of peroxycarboxylic acid or peroxy compound in the composition that can be detected by a suitable analytical technique, for example, by titration, chromatography, spectroscopy, oxidation-reduction probe, amperometrically, or similar peracid detection method.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3-1 $\log_{10}$. In this application, such a population reduction is the minimum acceptable for the processes.

Any increased reduction in population of microorganisms is an added benefit that provides higher levels of protection. For example, as set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2), a sanitizer should provide a 99.999% reduction (5 log order reduction) within 30 seconds at room temperature, 25±2° C., against several test organisms.

As used herein, the term "sterilant" refers to a physical or chemical agent or process capable of destroying all forms of life (including bacteria, viruses, fungi, and spores) on inanimate surfaces. One procedure is described in A.O.A.C. *Sporicidal Activity of Disinfectants*, Official Methods of Analysis of the Association of Official Analytical Chemists, paragraph 966.04 and applicable sections, $15^{th}$ Edition, 1990 (EPA Guideline 91-2).

As used herein, the term "antimicrobial composition" refers to a composition having the ability to cause greater than a 90% reduction (1-log order reduction) in the population of bacteria or spores of *Bacillus* species within 10 seconds at 60° C., using the above-mentioned *Germicidal and Detergent Sanitizing Action of Disinfectants* procedure. Preferably, *Bacillus cereus* or *Bacillus subtilis* are used in such procedure.

Also preferably, the antimicrobial compositions of the invention provide greater than a 99% reduction (2-log order reduction), more preferably greater than a 99.99% reduction (4-log order reduction), and most preferably greater than a 99.999% reduction (5-log order reduction) in such population within 10 seconds at 60° C. Preferably, the antimicrobial compositions of the invention also provide greater than a 99% reduction (2-log order reduction), more preferably greater than a 99.99% reduction (4-log order reduction), and most preferably greater than a 99.999% reduction (5-log order reduction) in the population of one or more additional organisms, such as the mold *Chaetomium funicola*. Because in their broadest sense these definitions for antimicrobial activity are different from some of the current governmental regulations, the use in connection with this invention of the term "antimicrobial" is not intended to indicate compliance with any particular governmental standard for antimicrobial activity.

As used herein, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. Preferably, the sporicidal compositions of the invention provide greater than a 99% reduction (2-log order reduction), more preferably greater than a 99.99% reduction (4-log order reduction), and most preferably greater than a 99.999% reduction (5-log order reduction) in such population within 10 seconds at 60° C.

As used herein, the term "sanitizer" refers to an agent that reduces the number of bacterial contaminants to safe levels as judged by public health requirements. Preferably, sanitizers for use in this invention will provide at least a 99.999% reduction (5-log order reduction) using the *Germicidal and Detergent Sanitizing Action of Disinfectants* procedure referred to above.

As used herein, the term "disinfectant" refers to an agent that kills all vegetative cells including most recognized pathogenic microorganisms, using the procedure described in A.O.A.C. *Use Dilution Methods*, Official Methods of Analysis of the Association of Official Analytical Chemists, paragraph 955.14 and applicable sections, 15th Edition, 1990 (EPA Guideline 91-2).

As used herein, the term "preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation. Sterilants, sanitizers, disinfectants, sporicides, virucides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act).

When applied to microbes (e.g., when applied to a surface containing microbes), the compositions of the invention exhibit antimicrobial action. The mechanism by which such action takes place is not completely understood. However, as shown in the Examples set out below, very rapid and substantially complete antimicrobial action can be attained.

As used herein, the term "phase" refers to a homogeneous fluid (e.g., liquid or gas) or solid portion that is present in or that can form in a fluid system. The term "phases" refers to the presence of more than one phase in a heterogeneous fluid system.

As used herein, the term "pseudo-stable" refers to a composition that forms a single phase when subjected to mild mixing or other agitation and retains that single phase for a sufficient period of time so that the composition can be applied to a surface, but which will promptly form two or more phases when left undisturbed. As used herein, the term "phase-splitting" refers to a single phase composition that forms at least two laminar phases promptly after being applied atop a generally horizontal surface or on a generally vertical surface, with a film containing a concentrated amount of antimicrobial solvent lying between the surface and a film containing a much lower amount of antimicrobial solvent. As used herein, the term "quasi-stable" refers to a composition having a clear or slightly cloudy appearance, that does not form a clear single-phase solution or microemulsion, and that does not undergo phase-splitting.

Two Solvent Antimicrobial Compositions

The present invention relates to antimicrobial compositions containing two solvents. A first solvent is present in a major portion, and a second solvent in a minor portion. The second solvent is typically insoluble or only sparingly soluble in the first solvent. Preferably, the first solvent includes or is a diluting solvent and the second solvent includes or is an antimicrobial solvent. Preferred antimicrobial solvents include mono- and diester dicarboxylates. Preferred diluting solvents include water. Preferred two solvent compositions form a clear single-phase solution. The two-solvent antimicrobial compositions can also include antimicrobial agent, stabilizer, wetting agent, chelant, buffering agent, cosolvent, hydrotrope, surfactant, or mixtures thereof.

Typically, the antimicrobial composition includes one or more antimicrobial agents in addition to antimicrobial solvent. The antimicrobial agent can be selected to be more soluble in the first solvent or in the second solvent. While not a requirement of the present invention, preferably, the antimicrobial agent is more soluble in the second solvent compared to the diluting solvent. Preferably, the antimicrobial agent preferentially dissolves, disperses, or migrates into the second solvent in preference to the diluting solvent. Preferably, the mixture of second solvent and antimicrobial agent preferentially accesses the microbe. For example, although not limiting to the present invention, it is believed that antimicrobial agents that can be uncharged in liquid compositions or that have more than 6 carbon atoms will preferentially partition into the second solvent compared to the diluting solvent. Antimicrobial agents having more than two carbon atoms will typically partially partition into the second solvent compared to the diluting solvent.

By way of further example, preferred antimicrobial agents and second solvents into which they, in some measure, partition include a peracid such as peroxyacetic acid and diester dicarboxylates such as DBE-3™, for example, peroxyoctanoic acid and dimethyl suberate, monoester peroxycarboxylic acids derived from diacids or diesters (e.g., such as adipic, succinic, glutaric, or malonic acid and mixtures thereof) and DBE-6™. Other examples can include halogen compounds such as an iodophor and dimethyl sebacate, or $ICl_x$ (x=1–4) and diester dicarboxylates such as DBE™, or $ClO_2$ and diester dicarboxylates such as DBE-6™.

Preferred antimicrobial agents include antimicrobial agents that can be considered oxidizing agents, such as halogen containing compounds, peroxides, and peroxycarboxylic acids. Preferred antimicrobial agents include antimicrobial agents that can be considered organic acidifying agents, such as aliphatic and aromatic carboxylic acids. Such preferred antimicrobial agents are described in additional detail hereinbelow.

In a preferred embodiment, the two solvent composition reduces the population of one or more microorganisms on food packaging, such as aseptic food or beverage, on pharmaceutical, packaging, on a health care surface, or in a health care environment.

For example, a preferred two solvent antimicrobial composition or two solvent ester peroxycarboxylic acid composition of the present invention is effective for killing one or more of the pathogenic or contaminating spore-forming bacteria or fungi associated with foods, beverages, pharmaceuticals, or their packaging or containers. Such fungi or bacteria include *Zygosaccharomyces bailii, Bacillus cereus, Bacillus subtilis*, and molds including *Chaetomium* spp., e.g., *Chaetomium funicola, Arthrinium*, and like genera; yeast, other molds, and the like. The compositions and methods of the present invention have activity against a wide variety of microorganisms such as Gram positive (for example, *Listeria monocytogenes*) and Gram negative (for example, *Escherichia coli*) bacteria, mycobacteria (such as that leading to tuberculosis), yeast, molds, bacterial spores, viruses, etc. The compositions and methods of the present invention, as described above, have activity against a wide variety of human pathogens including *Staphylococcus aureus, Pseudomonas aeruginosa*. The compositions and methods can kill a wide variety of microorganisms on a food, beverage, or pharmaceutical processing surface or equipment.

By way of further example, a preferred antimicrobial two solvent composition or two solvent ester peroxycarboxylic acid composition of the present invention of the present invention is effective for killing one or more of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold and the like. The compositions and methods of the present invention, as described above, have activity against a wide variety of human pathogens. The compositions and methods can kill a wide variety of microorganisms on a food processing surface, on the surface of a food product, or in water used for washing or processing of food product.

The preferred compositions include concentrate compositions and use compositions. The two-solvent antimicrobial compositions can be made and/or supplied as concentrates that are used as is or diluted with additional, or another, diluting solvent. The two-solvent antimicrobial compositions will likely be made and used as a use solution; either from the aforementioned concentrates or from individual raw materials. For example, a use composition can be made at the point of use from individual ingredients or from a concentrate mixture. For example, a two solvent antimicrobial composition can be used as is or mixed with a diluting solvent or gas. Water is a preferred diluting solvent. Preferred diluting gasses include carbon dioxide, nitrogen, oxygen, air, or mixtures thereof. Typically, an antimicrobial concentrate composition can be diluted with a solvent, gas, or steam, for example with water, to form an antimicrobial use composition. In a preferred embodiment, the concentrate composition is diluted into water employed for washing or processing a food, beverage, or pharmaceutical, or a container or equipment employed in producing foods, beverages, or pharmaceuticals, or for filling food or beverage or pharmaceutical containers.

Preferred methods of the present invention include some form of mixing, particularly as a concentrate is, or individual ingredients are, added to water to make the use composition. Mixing can occur as a separate step or as part of applying use composition to an object. Preferred methods for mixing and/or applying include agitating, dipping, immersing, flooding, aspirating, pumping, spraying, fogging, annular misting or spraying, or sonicating. Preferred methods include water systems that have some agitation, spraying, fogging, re-circulation, or other mixing of the solution.

Ranges of Ingredients for Certain Embodiments of Two Solvent Antimicrobial Compositions Typical two-solvent antimicrobial compositions include about 0.001 wt-% to about 95 wt-% antimicrobial solvent, about 5 wt-% to about 99.999 wt-% diluting solvent, and, optionally, about 0.001 wt-% to about 65 wt-% antimicrobial agent. Preferred two-solvent antimicrobial compositions include about 0.01 wt-% to about 60 wt-% antimicrobial solvent, about 50 wt-% to about 99.8 wt-% diluting solvent, and, optionally, about 0.01 wt-% to about 25 wt-% antimicrobial agent. Preferred two-solvent antimicrobial compositions include about 0.1 wt-% to about 15 wt-% antimicrobial solvent, about 60 wt-% to about 99.5 wt-% diluting solvent, and, optionally, about 0.1 wt-% to about 15 wt-% antimicrobial agent. These compositions can also include one or more of stabilizers, catalysts, buffers, acidulants, and the like. These compositions can include the stated amounts or ranges not modified by about.

Preferred concentrate two-solvent antimicrobial compositions include about 10 wt-% to about 50 wt-% antimicrobial solvent, about 10 wt-% to about 80 wt-% diluting solvent, and, optionally, about 2.5 wt-% to about 25 wt-% antimicrobial agent. These concentrate compositions can also include one or more of stabilizer, catalyst, buffer, acidulant, and the like. These concentrate compositions can include the stated amounts or ranges not modified by about.

Typically, for use, two-solvent antimicrobial compositions include about 0.001 wt-% to about 20 wt-% antimicrobial solvent, about 80 wt-% to about 99.999 wt-% diluting solvent, and, optionally, about 0.001 wt-% to about 10 wt-% antimicrobial agent. Preferred two-solvent antimicrobial use compositions include about 0.01 wt-% to about 10 wt-% antimicrobial solvent, about 85 wt-% to about 99.8 wt-% diluting solvent, and, optionally, about 0.01 wt-% to about 5 wt-% antimicrobial agent. Preferred two-solvent antimicrobial use compositions include about 0.1 wt-% to about 5 wt-% antimicrobial solvent, about 93 wt-% to about 99.9 wt-% diluting solvent, and, optionally, about 0.08 wt-% to about 2.5 wt-% antimicrobial agent. These use compositions can also include one or more of stabilizer, catalyst, buffer, acidulant, and the like. These use compositions can include the stated amounts or ranges not modified by about.

Typical two-solvent antimicrobial compositions can include about 0.1 wt-% to about 60 wt-% antimicrobial solvent, about 10 wt-% to about 99.999 wt-% diluting solvent, and about 0.0025 wt-% to about 30 wt-% antimicrobial agent. Preferred two-solvent antimicrobial compositions can include about 0.1 wt-% to about 20 wt-% antimicrobial solvent, about 30 wt-% to about 99.99 wt-% diluting solvent, and about 0.007 wt-% to about 3 wt-% antimicrobial agent. Preferred two-solvent antimicrobial compositions can include about 0.25 wt-% to about 15 wt-% antimicrobial solvent, about 90 wt-% to about 99 wt-% diluting solvent, and about 0.01 wt-% to about 6 wt-% antimicrobial agent. Preferred two-solvent antimicrobial compositions can include about 0.5 wt-% to about 6 wt-% antimicrobial solvent, about 95 wt-% to about 99 wt-% diluting solvent, and about 0.025 wt-% to about 3 wt-% antimicrobial agent.

Typical two-solvent antimicrobial compositions can include about 0.1 wt-% to about 60 wt-% antimicrobial solvent, preferably about 0.3 wt-% to about 20 wt-% antimicrobial solvent, preferably about 0.5 wt-% to about 15 wt-% antimicrobial solvent, preferably about 1 wt-% to about 6 wt-% antimicrobial solvent. Preferred antimicrobial solvents include benzyl alcohol and diester dicarboxylates, such as DBE-3™, DBE-6™, dimethyl suberate. Typical two-solvent antimicrobial compositions can include about 10 wt-% to about 99.999 wt-% diluting solvent, preferably about 30 wt-% to about 99.99 wt-% diluting solvent, preferably about 90 wt-% to about 99 wt-% diluting solvent, preferably about 95 wt-% to about 99 wt-% diluting solvent. Preferred diluting solvents include water. Typical two-solvent antimicrobial compositions can include about 0.0025 wt-% to about 30 wt-% antimicrobial agent, preferably about 0.007 wt-% to about 3 wt-% antimicrobial agent, preferably about 0.01 wt-% to about 6 wt-% antimicrobial agent, preferably about 0.025 wt-% to about 3 wt-% antimicrobial agent. Preferred antimicrobial agents include halogen containing antimicrobial agents, carboxylic acids, and peroxycarboxylic acids.

Certain embodiments of the two solvent antimicrobial compositions include the ranges of ingredients in this table:

| | Antimicrobial Solvent | Diluting Solvent | Antimicrobial Agent |
|---|---|---|---|
| Use Compositions | | | |
| Typical | 0.001–20 | 80–99.999 | 0.001–10 |
| Preferred | 0.01–10 | 85–99.99 | 0.01–5 |
| More preferred | 0.08–5 | 92.5–99.9 | 0.1–2.5 |
| Concentrates | | | |
| Typical | 0.1–99.9 | 5–99 | 1–60 |
| Preferred | 1–60 | 5–95 | 1–40 |
| More Preferred | 10–50 | 10–80 | 2.5–25 |

Ranges for Certain Embodiments of Two Solvent Compositions Including Peroxycarboxylic Acids Preferred two-solvent antimicrobial compositions can include about 0.01 wt-% to about 95 wt-% diester dicarboxylate, about 5 wt-% to about 99.999 wt-% water, and about 0.01 wt-% to about 35 wt-% peroxycarboxylic acid. Such preferred compositions can also include 0.01 wt-% to about 75 wt-% hydrogen peroxide and, optionally, about 0.00001 wt-% to about 5 wt-% stabilizer or catalyst, about 0.001 wt-% to about 10 wt-% surfactant, and/or about 0.001 wt-% to about 10 wt-% buffer. Preferred two-solvent antimicrobial compositions include about 0.1 wt-% to about 90 wt-% diester dicarboxylate, about 10 wt-% to about 99.9 wt-% water, and about 0.05 wt-% to about 15 wt-% peroxycarboxylic acid. Such preferred compositions can also include 0.03 wt-% to about 65 wt-% hydrogen peroxide and, optionally, about 0.01 wt-% to about 3 wt-% stabilizer or catalyst, about 0.01 wt-% to about 5 wt-% surfactant, and/or about 0.01 wt-% to about 5 wt-% buffer. Preferred two-solvent antimicrobial compositions include about 0.2 wt-% to about 65 wt-% diester dicarboxylate, about 35 wt-% to about 99.2 wt-% water, and about 0.08 wt-% to about 11 wt-% peroxycarboxylic acid. Such preferred compositions can also include 0.05 wt-% to about 55 wt-% hydrogen peroxide and, optionally, about 0.1 wt-% to about 2 wt-% stabilizer or catalyst, about 0.1 wt-% to about 2 wt-% surfactant, and/or about 0.1 wt-% to about 2 wt-% buffer. These compositions can include the stated amounts or ranges not modified by about.

Preferred concentrate two-solvent antimicrobial compositions include about 10 wt-% to about 50 wt-% diester dicarboxylate, about 10 wt-% to about 80 wt-% water, and about 2.5 wt-% to about 11 wt-% peroxycarboxylic acid. Such preferred concentrate compositions can also include about 1 wt-% to about 2 wt-% stabilizer or catalyst, about 1 wt-% to about 2 wt-% surfactant, and/or about 1 wt-% to about 2 wt-% buffer. These concentrate compositions can include the stated amounts or ranges not modified by about.

Preferably, for use, two-solvent antimicrobial compositions can include about 0.001 wt-% to about 20 wt-% diester dicarboxylate, about 80 wt-% to about 99.99 wt-% water, and about 0.01 wt-% to about 10 wt-% peroxycarboxylic acid. Such preferred use compositions can also include 0.003 wt-% to about 25 wt-% hydrogen peroxide and, optionally, about 0.001 wt-% to about 5 wt-% stabilizer or catalyst, about 0.001 wt-% to about 10 wt-% surfactant, and/or about 0.001 wt-% to about 10 wt-% buffer. Preferred two-solvent antimicrobial use compositions include about 0.1 wt-% to about 10 wt-% diester dicarboxylate, about 85 wt-% to about 99.99 wt-% water, and about 0.01 wt-% to about 5 wt-% peroxycarboxylic acid. Such preferred use compositions can also include 0.03 wt-% to about 20 wt-% hydrogen peroxide and, optionally, about 0.001 wt-% to about 3 wt-% stabilizer or catalyst, about 0.001 wt-% to about 5 wt-% surfactant, and/or about 0.001 wt-% to about 5 wt-% buffer. Preferred two-solvent antimicrobial use compositions include about 0.1 wt-% to about 5 wt-% diester dicarboxylate, about 93 wt-% to about 99.9 wt-% water, and about 0.08 wt-% to about 2.5 wt-% peroxycarboxylic acid. Such preferred use compositions can also include 0.08 wt-% to about 10 wt-% hydrogen peroxide and, optionally, about 0.01 wt-% to about 2 wt-% stabilizer or catalyst, about 0.01 wt-% to about 2 wt-% surfactant, and/or about 0.01 wt-% to about 2 wt-% buffer. These use compositions can include the stated amounts or ranges not modified by about.

For example, the two-solvent antimicrobial composition can include up to 95 wt-% diester dicarboxylate, up to 35 wt-% active peroxycarboxylic acid, up to 75 wt-% hydrogen peroxide, up to 99.99 wt-% water, plus optional additives. Preferably, the two-solvent antimicrobial composition includes up to 65 wt-% diester dicarboxylate, up to 15 wt-% active peroxycarboxylic acid, up to 45 wt-% hydrogen peroxide, up to 99.5 wt-% water, plus optional additives. Preferably the two-solvent antimicrobial composition includes up to 45 wt-% diester dicarboxylate, up to 10 wt-% active peroxycarboxylic acid, up to 15 wt-% hydrogen peroxide, up to 99 wt-% water, plus optional additives. These compositions can include the stated amounts or ranges not modified by about.

For example, for use, the two-solvent antimicrobial composition can include up to 20 wt-% diester dicarboxylate, up to 10 wt-% active peroxycarboxylic acid, up to 60 wt-% hydrogen peroxide, up to 99.99 wt-% water, plus optional additives. Preferably, the two-solvent antimicrobial use composition includes up to 10 wt-% diester dicarboxylate, up to 5 wt-% active peroxycarboxylic acid, up to 20 wt-% hydrogen peroxide, up to 99.5 wt-% water, plus optional additives. Preferably the two-solvent antimicrobial use composition includes up to 5 wt-% diester dicarboxylate, up to 2.5 wt-% active peroxycarboxylic acid, up to 10 wt-% hydrogen peroxide, up to 99 wt-% water, plus optional additives. These use compositions can also include one or more of stabilizer, catalyst, buffer, acidulant, and the like. These compositions can include the stated amounts or ranges not modified by about.

For example, the two-solvent antimicrobial use composition can include about 0.001 wt-% to about 95 wt-% diester dicarboxylate, preferably about 0.05 wt-% to about 5 wt-% diester dicarboxylate, more preferably about 0.1 wt-% to about 3 wt-% diester dicarboxylate. For example, the two-solvent antimicrobial use composition can include about 0.01 wt-% to about 35 wt-% active peroxycarboxylic acid, preferably about 0.05 wt-% to about 5 wt-% active peroxycarboxylic acid, more preferably about 0.08 wt-% to about 2.5 wt-% active peroxycarboxylic acid. For example, the two-solvent antimicrobial composition can include about 0.01 wt-% to about 25 wt-% hydrogen peroxide, preferably about 0.05 wt-% to about 5 wt-% hydrogen peroxide, more preferably about 0.1 wt-% to about 3 wt-% hydrogen peroxide. For example, the two-solvent antimicrobial use composition can include about 0.001 wt-% to about 15 wt-% stabilizer, preferably about 0.01 wt-% to about 3 wt-% stabilizer, more preferably about 0.1 wt-% to about 2 wt-% stabilizer. For example, the two-solvent antimicrobial composition can include about 0.001 wt-% to about 10 wt-% buffering agents, preferably about 0.01 to about 5 wt-% buffering agents, more preferably about 0.1 wt-% to about 2 wt-% buffering agents. For example, the two-solvent antimicrobial use composition can include about 50 to about 99.999 wt-% water, preferably about 70 to about 99.8 wt-% water, more preferably about 85 to about 99.5 wt-% water. These compositions can include the stated amounts or ranges not modified by about.

Ranges for Certain Embodiments of Two Solvent Compositions Including Carboxylic Acids Employing carboxylic acid antimicrobial agents, typical two-solvent antimicrobial compositions can include about 0.001 wt-% to about 99.9 wt-% antimicrobial solvent, about 1 wt-% to about 99.999 wt-% diluting solvent, and about 0.001 wt-% to about 85 wt-% carboxylic acid antimicrobial agent. For example, a preferred two-solvent antimicrobial composition can include about 0.1 wt-% to about 95 wt-% antimicrobial solvent, about 5 wt-% to about 99.9 wt-% diluting solvent, and about 0.001 wt-% to about 25 wt-% carboxylic acid antimicrobial agent. For example, the two-solvent antimicrobial composition can include about 0.001 wt-% to about 15 wt-% diester dicarboxylate, about 70 wt-% to about 99.9 wt-% water, and about 0.01 wt-% to about 10 wt-% carboxylic acid. Such compositions can optionally include up to about 30 wt-% of additives such as acidulants, buffers, co-solvents, surfactants, and the like. The compositions can include the stated amounts or ranges not modified by about.

Employing carboxylic acid antimicrobial agents, preferred concentrate two-solvent antimicrobial composition can include about 10 wt-% to about 50 wt-% diester dicarboxylate, about 10 wt-% to about 80 wt-% water, and about 2.5 wt-% to about 25 wt-% carboxylic acid. Such concentrate compositions can optionally include up to about 30 wt-% of additives such as acidulants, buffers, co-solvents, surfactants, and the like. The compositions can include the stated amounts or ranges not modified by about.

Employing carboxylic acid antimicrobial agents, typical two-solvent antimicrobial use compositions can include about 0.001 wt-% to about 20 wt-% antimicrobial solvent, about 80 wt-% to about 99.999 wt-% diluting solvent, and about 0.001 wt-% to about 10 wt-% carboxylic acid antimicrobial agent. For example, a preferred two-solvent antimicrobial use composition can include about 0.01 wt-% to about 10 wt-% antimicrobial solvent, about 85 wt-% to about 99.99 wt-% diluting solvent, and about 0.01 wt-% to about 5 wt-% carboxylic acid antimicrobial agent. For example, the two-solvent antimicrobial use composition can include about 0.1 wt-% to about 5 wt-% diester dicarboxylate, about 93 wt-% to about 99.9 wt-% water, and about 0.08 wt-% to about 2.5 wt-% carboxylic acid. Such compositions can optionally include up to about 30 wt-% of additives such as acidulants, buffers, co-solvents, surfactants, and the like. The compositions can include the stated amounts or ranges not modified by about.

Ranges for Certain Embodiments of Two Solvent Compositions Including Halogen Containing Antimicrobial Agents Employing halogen containing (e.g., $ClO_2$, $Cl_2$, $^-OCl$, HOCl, HOBr, $^-OBr$, $Br_2$, ICl or IBr or salts of $IBr_x$ or $ICl_x$ x=1–4, $I_x$ x=2–9) antimicrobial agents, typical two-solvent antimicrobial compositions can include about 0.001 wt-% to about 99.9 wt-% antimicrobial solvent, about 1 wt-% to about 99.999 wt-% diluting solvent, and about 0.001 wt-% to about 85 wt-% halogen containing antimicrobial agent. For example, a preferred two-solvent antimicrobial composition can include about 0.1 wt-% to about 95 wt-% antimicrobial solvent, about 5 wt-% to about 99.9 wt-% diluting solvent, and about 0.001 wt-% to about 25 wt-% halogen containing antimicrobial agent. For example, the two-solvent antimicrobial composition can include about 0.001 wt-% to about 15 wt-% diester dicarboxylate, about 70 wt-% to about 99.9 wt-% water, and about 0.01 wt-% to about 10 wt-% halogen containing antimicrobial agent. Such compositions can optionally include up to about 30 wt-% of additives such as acidulants, buffers, co-solvents, surfactants, and the like. The compositions can include the stated amounts or ranges not modified by about.

Employing halogen containing antimicrobial agents, preferred concentrate two-solvent antimicrobial composition can include about 10 wt-% to about 50 wt-% diester dicarboxylate, about 10 wt-% to about 80 wt-% water, and about 2.5 wt-% to about 25 wt-% halogen containing antimicrobial agent. Such concentrate compositions can optionally include up to about 30 wt-% of additives such as acidulants, buffers, co-solvents, surfactants, and the like. The compositions can include the stated amounts or ranges not modified by about.

Employing halogen containing antimicrobial agents, typical two-solvent antimicrobial use compositions can include about 0.001 wt-% to about 20 wt-% antimicrobial solvent, about 80 wt-% to about 99.999 wt-% diluting solvent, and about 0.001 wt-% to about 10 wt-% halogen containing antimicrobial agent. For example, a preferred two-solvent antimicrobial use composition can include about 0.01 wt-% to about 10 wt-% antimicrobial solvent, about 85 wt-% to about 99.99 wt-% diluting solvent, and about 0.01 wt-% to about 5 wt-% halogen containing antimicrobial agent. For example, the two-solvent antimicrobial use composition can include about 0.1 wt-% to about 5 wt-% diester dicarboxylate, about 92.5 wt-% to about 99.9 wt-% water, and about 0.08 wt-% to about 2.5 wt-% halogen containing antimicrobial agent. Such compositions can optionally include up to about 30 wt-% of additives such as acidulants, buffers, co-solvents, surfactants, and the like. The compositions can include the stated amounts or ranges not modified by about.

Diluting Solvent

A variety of fluids can be used as the diluting solvent, including water (e.g. liquid water, ice, or steam); condensed gases and other sub- or supercritical fluids (e.g., $CO_2$); perchloroethylene; oils such as silicone oils (e.g., siloxanes), gear oils, transaxle oils, mineral oils or vegetable oils; and carboxylic esters such as methyl soyate; glycols; organic acids; peroxides; and inorganic acids. Mixtures of diluting solvents can be used if desired. Especially useful oils include food grade or food-derived oils, flavorings, or fragrance oils. Preferred two solvent antimicrobial compositions can include water, glycols, $CO_2$, organic acids, peroxides, and inorganic acids as diluting solvent, more preferably water, glycols, and organic acids as diluting solvent, more preferably water as diluting solvent.

Preferably, the diluting solvent includes water, consists essentially of water, or consists of water, in its liquid or vapor forms, preferably in its liquid form. The remainder of this specification will primarily discuss the use of water in its liquid form as the diluting solvent, it being understood that other suitable fluids could be added to or substituted for water in its liquid form if desired.

Typical two solvent antimicrobial compositions can include from about 5 wt-% to about 99.999 wt-% diluting solvent, preferably about 50 wt-% to about 99.99 wt-% diluting solvent, preferably about 75 wt-% to about 99.9 wt-% diluting solvent, and preferably about 85 wt-% to about 99.5 wt-% diluting solvent. Concentrate two solvent antimicrobial compositions preferably include from about 10 wt-% to about 80 wt-% diluting solvent. Typically, for use, two solvent antimicrobial compositions can include from about 80 wt-% to about 99.999 wt-% diluting solvent, preferably about 85 wt-% to about 99.99 wt-% diluting solvent, preferably about 92.5 wt-% to about 99.9 wt-% diluting solvent. These compositions can include the stated amounts or ranges not modified by about.

Antimicrobial Solvent

The compositions of the invention can contain a variety of antimicrobial solvents. The antimicrobial solvent preferably is insoluble, or only sparingly soluble, in the diluting solvent. Thus for compositions containing water as the diluting solvent, and for concentrates intended to be diluted with water, the antimicrobial solvent preferably will have a water solubility less than about 15 wt-%, more preferably less than about 10 wt-%, and most preferably less than about 5 wt-%, or any of these amounts not modified by about.

Any of a variety of solvents can be useful as antimicrobial solvents in the compositions. Suitable antimicrobial solvents include acetamidophenol; acetanilide (water solubility <1%); acetophenone (water solubility <1%); [2-acetyl-1-methylpyrrole; benzyl acetate water solubility <1%); benzyl alcohol (water solubility ~4%); benzyl benzoate (water solubility <1%); benzyloxyethanol (water solubility <1%); ethers or hydroxyethers such as ethylene glycol phenyl ether (water solubility 2.3%; commercially available as DOWANOL EPH™ from Dow Chemical Co.); and propylene glycol phenyl ether (water solubility 1.1%; commercially available as DOWANOL PPH™ from Dow Chemical Co.); essential oils (e.g., benzaldehyde, pinenes, terpineols, terpinenes, carvone, cinnamealdehyde, borneol and its esters, citrals, ionenes, jasmine oil, limonene, dipentene, linalool and its esters); diester dicarboxylates (e.g., dibasic esters) such as dimethyl adipate, dimethyl succinate, dimethyl glutarate (including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dimethyl sebacates, dimethyl pimelates, dimethyl suberates; dialkyl carbonates such as dimethyl carbonate, diethyl carbonate, dipropyl carbonate, diisopropyl carbonate, and dibutyl carbonate; $C_{1-16}$ protonated carboxylic acids such as 2-ethyl-1-hexanoic acid, butyric acid, octanoic acid, heptanoic acid, nonanoic acid, and decanoic acid; $C_{1-12}$ organic anhydrides such as acetic anhydride, succinic anhydride, phthalic anhydride, maleic anhydride, and alkyl or alkenyl succinic anhydrides; organo-nitriles such as acetonitrile and benzonitrile; organo-phosphates and phosphonates such as tributyl phosphate, tripropyl phosphate, 2-ethyl-1-hexyl phosphate; and phthalate esters such as dibutyl phthalate, diethylhexyl phthalate, and diethyl phthalate. The water solubilities noted above are room temperature values available from standard references. Benzyl alcohol, phenylethanol, essential oils, diester dicarboxylates, dialkyl carbonates, ethylene glycol phenyl ether and propylene glycol phenyl ether are preferred antimicrobial solvents. More preferred antimicrobial solvents include diester dicarboxylates. Mixtures of antimicrobial solvents can be used if desired.

The antimicrobial solvent can be selected based upon the characteristics of the surface and microbes to which the antimicrobial composition will be applied and upon the nature of any coating, soil or other material that will be contacted by the antimicrobial composition and optionally removed from the surface. Polar solvents, and solvents that are capable of hydrogen bonding typically will perform well on a variety of surfaces and microbes and thus are preferred. Preferably, the antimicrobial solvent also has a high flashpoint (e.g., greater than about 30° C., more preferably greater than about 50° C., and most preferably greater than about 100° C.), low odor, and low human and animal toxicity.

A most preferred solvent is compatible as an indirect or direct food additive or substance; especially those described in the Code of Federal Regulations (CFR), Title 21—Food and Drugs, parts 170 to 186 (which is incorporated herein by reference). The compositions of the invention should contain sufficient antimicrobial solvent to provide the desired rate and type of microbial reduction.

Preferred two solvent antimicrobial compositions include a diester dicarboxylate, such as DBE, DBE-3, DBE-4, DBE-5, DBE-6, DBE-9, DBE-IB, and DBE-ME, as antimicrobial solvent. Preferred diester dicarboxylate antimicrobial solvents include DBE-3, DBE-6, dimethyl pimelate, dimethyl suberate, or mixtures thereof. Preferred two solvent antimicrobial compositions can include symmetrical or mixed diester of adipic acid, pimelic acid, suberic acid, or mixtures thereof as diester dicarboxylate antimicrobial solvent. Preferred two solvent antimicrobial compositions can include symmetrical and mixed diesters of adipic acid pimelic acid, or suberic acid, or mixtures thereof as diester dicarboxylate antimicrobial solvent.

Typical two solvent antimicrobial compositions can include from about 0.01 wt-% to about 60 wt-% antimicrobial solvent, preferably about 0.05 wt-% to about 15 wt-% antimicrobial solvent, preferably about 0.08 wt-% to about 5 wt-% antimicrobial solvent, and preferably about 0.1 wt-% to about 3 wt-% antimicrobial solvent. Concentrate two solvent antimicrobial compositions preferably include from about 2 wt-% to about 50 wt-% antimicrobial solvent. Typically, for use, two solvent antimicrobial compositions can include from about 0.001 wt-% to about 20 wt-% antimicrobial solvent, preferably about 0.01 wt-% to about 10 wt-% antimicrobial solvent, and preferably about 0.08 wt-% to about 5 wt-% antimicrobial solvent. The compositions can include the stated amounts or ranges not modified by about.

Diester Dicarboxylates

As used herein, diester dicarboxylate refers to molecules having the formula:

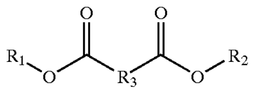

In this formula, $R_1$, $R_2$, and $R_3$ can independently be any of a wide variety of organic groups (e.g., alkyl, linear or cyclic, aromatic or saturated) or substituted organic groups (e.g., with one or more heteroatoms or organic groups).

Preferred diester dicarboxylates include alkyl diester dicarboxylates, preferably having the formula:

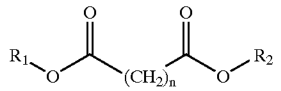

where $R_1$ and $R_2$ represent independently an alkyl group having from 1 to 8 carbons, preferably 1 to 6, preferably 1 to 3, and n is 0 to 10, preferably 1 to 8, preferably 1 to 6. The alkyl group can be either straight chain or branched. Preferably, $R_1$ and $R_2$ are independently a methyl, ethyl, propyl (n-, iso-), butyl (n-, iso-, tert-), n-amyl, n-hexyl, or 2-ethylhexyl group. Preferably, n is 2, 3, 4, 5, or 6.

In one preferred embodiment, the composition of the present invention includes a mixture of alkyl diester dicarboxylates in which n is 2, 3, and 4. Such a mixture includes diesters of peroxyadipic, peroxyglutaric, and peroxysuccinic acids. In another preferred embodiment, a majority of the alkyl diester dicarboxylates in the composition has n equal to 3 or 4.

In yet another preferred embodiment, a majority of the alkyl diester dicarboxylates in the composition has n equal to 5, 6, or 7. In a preferred embodiment, $R_1$ and $R_2$ are independently a $C_1$–$C_8$ alkyl. In a preferred embodiment, n is 1, 2, 3, or 4. Most preferably, $R_1$ and $R_2$ are independently a $C_1$ alkyl, $C_3$ alkyl, $C_4$ alkyl, and n is 2, 3, 4, or 5.

In another preferred embodiment, $R_1$ and $R_2$ are independently a $C_5$–$C_8$ alkyl and n is 5, 6, or 7. In another preferred embodiment, $R_1$ and $R_2$ are independently a $C_1$–$C_2$ alkyl and n is 5, 6, or 7.

Alkyl diester dicarboxylates useful in this invention include all symmetrical and mixed diesters of oxalic acid, malonic acid, succinic acid, glutaric acid, adipic acid, pimelic acid, suberic acid, or sebacic acid (or mixtures thereof) with methanol, ethanol, propanol (e.g., n-propanol or isopropanol), butanol (e.g., n-butanol, iso-butanol, or tert-butanol), amyl alcohol (e.g., n-pentanol, iso-pentanol, sec-pentanol, or tert-pentanol), hexanol (e.g., n-hexanol, iso-hexanol, sec-hexanol, or tert-hexanol), octanol (e.g., n-octanol, iso-octanol, sec-octanol, or tert-octanol) or mixtures thereof.

Such alkyl diester dicarboxylates include dimethyl oxalate, methyl ethyl oxalate, methyl propyl oxalate, methyl butyl oxalate, dimethyl malonate, methyl ethyl malonate, methyl propyl malonate, methyl butyl malonate, dimethyl succinate, methyl ethyl succinate, methyl propyl succinate, methyl butyl succinate, dimethyl glutarate, methyl ethyl glutarate, methyl propyl glutarate, methyl butyl glutarate, dimethyl adipate, methyl ethyl adipate, methyl propyl adipate, methyl butyl adipate, dimethyl pimelate, methyl ethyl pimelate, methyl propyl pimelate, methyl butyl pimelate, dimethyl suberate, methyl ethyl suberate, methyl propyl suberate, methyl butyl suberate, dimethyl sebacate, methyl ethyl sebacate, methyl propyl sebacate, methyl butyl sebacate, diethyl oxalate, ethyl propyl oxalate, ethyl butyl oxalate, diethyl malonate, ethyl propyl malonate, ethyl butyl malonate, diethyl succinate, ethyl propyl succinate, ethyl butyl succinate, diethyl glutarate, ethyl propyl glutarate, ethyl butyl glutarate, diethyl adipate, ethyl propyl adipate, ethyl butyl adipate, diethyl pimelate, ethyl propyl pimelate, ethyl butyl pimelate, diethyl suberate, ethyl propyl suberate, ethyl butyl suberate, diethyl sebacate, ethyl propyl sebacate, ethyl butyl sebacate, dipropyl oxalate, propyl butyl oxalate, dipropyl malonate, propyl butyl malonate, dipropyl succinate, propyl butyl succinate, dipropyl glutarate, propyl butyl glutarate, dipropyl adipate, propyl butyl adipate, dipropyl pimelate, propyl butyl pimelate, dipropyl suberate, propyl butyl suberate, dipropyl sebacate, propyl butyl sebacate, dibutyl oxalate, dibutyl malonate, dibutyl succinate, dibutyl glutarate, dibutyl adipate, dibutyl pimelate, dibutyl suberate, dibutyl sebacate, diamyl succinate, diamyl glutarate, diamyl adipate, diamyl pimelate, diamyl suberate, diamyl sebacate, dihexyl succinate, dihexyl glutarate, dihexyl adipate, dihexyl sebacate, dioctyl succinate, dioctyl glutarate, dioctyl adipate, dioctyl pimelate, dioctyl suberate, dioctyl sebacate, or mixtures thereof. In these esters propyl can be n- or iso-propyl; butyl can be n-, iso-, or tert-butyl; amyl can be n-, sec-, iso-, tert-amyl; hexyl can be n-, sec-, iso-, tert-hexyl; and octyl can be n-, iso-, sec-, tert-octyl, or 2-ethylhexyl-, or a mixture thereof.

Surprisingly, two solvent antimicrobial compositions including certain diester dicarboxylates show greater activity than compositions of certain other diester dicarboxylates. In particular, diester dicarboxylates derived from carboxylic acids having two carboxyl groups separated by 2 to 6 carbon atoms show greater antimicrobial activity. Preferred diester dicarboxylates are derived from carboxylic acids having two carboxyl groups separated by 3, 4, 5, or 6 carbon atoms, preferably 4, 5, or 6 carbon atoms, preferably 6 carbon atoms. Such preferred diester dicarboxylates include diesters of adipic acid, glutaric acid, pimelic acid, or suberic acid; preferably of adipic acid, pimelic acid, or suberic acid; more preferably of suberic acid or adipic acid.

In particular, diester dicarboxylates derived from alcohols having 1 to 2 carbon atoms show greater antimicrobial activity, particularly when the dicarboxylic moiety has 4 to 10 carbons. Preferred diester dicarboxylates are derived from alcohols having 1, 2, 3, or 4 carbon atoms, preferably 1 or 2 carbon atoms, preferably 1 carbon atom. Such preferred diester dicarboxylates include diesters of adipic, glutaric, succinic, pimelic or suberic acids. The esters can be symmetrical or mixed esters of methanol, ethanol, propanol, isopropanol, butanol, sec-butanol, t-butanol, amyl alcohol, hexanol, 2-ethylhexanol; preferably methanol, ethanol, or iso-butanol; preferably methanol or ethanol.

In particular, diester dicarboxylates having a total of 5 to 22 carbon atoms show greater antimicrobial activity. Preferred diester dicarboxylates have 6 to 12 carbon atoms, preferably 8 to 10 carbon atoms, and more preferably 9 or 10 carbon atoms. Such preferred diester dicarboxylates include methyl and ethyl diesters of adipic acid, glutaric acid, pimelic acid, suberic acid, or mixtures thereof, preferably esters of adipic acid, pimelic acid, suberic acid or mixtures thereof, preferably esters of pimelic acid, suberic acid, or mixtures thereof.

The methods and compositions of the present invention can also include mixtures of diester dicarboxylates known as dibasic esters and available under the trade designations DBE, DBE-3, DBE-4, DBE-5, DBE-6, DBE-9, DBE-IB, and DBE-ME from Dupont Nylon. These "DBEs" include single isolates or mixtures of species such as dimethyl adipate, dimethyl succinate, dimethyl glutarate, and diisobutyl adipate, diisobutyl succinate, and diisobutyl glutarate. Other diester dicarboxylates, such as dioctyl sebacate, bis-[2-ethylhexyl] sebacate, diamyl sebacate, dimethyl pimelate, and dimethyl suberate, are also commercially available in relatively pure form. These DBEs and the sebacate esters are preferred, in part, since they are commercially and economically available. Additional suitable diester dicarboxylates (or dibasic esters) include dimethyl malonate, dimethyl sebacate, diethyl adipate, diethyl succinate, diethyl glutarate, dibutyl succinate, and dibutyl glutarate; dialkyl carbonates such as dimethyl carbonate, diethyl carbonate, dipropyl carbonate, diisopropyl carbonate, and dibutyl carbonate.

Typical two solvent antimicrobial compositions as use or concentrate compositions or as mixed from individual ingredients at the point of use, can include about 0.001 wt-% to about 85 wt-% diester dicarboxylate, preferably about 0.05 wt-% to about 5 wt-% diester dicarboxylate, more preferably about 0.1 wt-% to about 3 wt-% diester dicarboxylate. Typical concentrate two solvent antimicrobial compositions can include about 10 wt-% to about 50 wt-% diester dicarboxylate. Typically, for use, two solvent antimicrobial compositions can include about 0.001 wt-% to about 50 wt-% diester dicarboxylate, preferably about 0.01 wt-% to about 10 wt-% diester dicarboxylate, more preferably about 0.08 wt-% to about 5 wt-% diester dicarboxylate. These compositions can include the stated amounts or ranges not modified by about.

Antimicrobial Agent

The antimicrobial compositions of the invention preferably contain an antimicrobial agent. Suitable antimicrobial agents include carboxylic acids, diacids, or triacids (e.g., formic acid, acetic acid, butyric acid, heptanoic acid, octanoic acid, nonanoic acid, decanoic acid, salicylic acid, mandelic acid, succinic acid, adipic acid, glutaric acid, EDTA and citric acid), carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides, iodine, interhalides, polyhalides, hypochlorite salts, hypochlorous acid, hypobromite salts, hypobromous acid, chloro- and bromo-hydantoins, chlorine dioxide, and sodium chlorite), active oxygen compounds including hydrogen peroxide, a percarbonate, a perborate, a persulfate, or isolated or equilibrium derived or isolated peroxycarboxylic acids such as chloroperbenzoic acids, peroxyacetic acid, peroxyheptanoic acid, peroxyoctanoic acid, peroxydecanoic acid, peroxyformic acid, peroxycitric acid, peroxyglycolic acid, peroxylactic acid, peroxybenzoic acid, and monoester peracids derived from diacids or diesters (e.g., such as adipic, succinic, glutaric, or malonic acid and mixtures thereof), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$–$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection.

Preferred antimicrobial agents include antimicrobial agents that can be considered oxidizing agents. Preferred oxidizing antimicrobial agents include halogen containing compounds and peroxycarboxylic acids. Preferred halogen containing compounds include elemental halogens, polyhalides, and halogen oxides (e.g., NaOCl, HOCl, HOBr, $ClO_2$), and the like. Preferred halogen oxides include hypochlorous acid (or its salts), chlorine dioxide, hypobromous acid (or its salts). Preferred halogen containing compounds also include an interhalide such as iodine monochloride, iodine dichloride, iodine trichloride, iodine tetrachloride, bromine chloride, iodine monobromide, or iodine dibromide. Preferred peroxycarboxylic acids include peroxyacetic acid, peroxyformic acid, peroxyoctanoic acid, and monoester peroxy dicarboxylic acids.

Preferred antimicrobial agents include antimicrobial agents that can be considered organic acidifying agents. Preferred organic acidifying antimicrobial agents include aliphatic and aromatic carboxylic acids. Preferred aliphatic or aromatic carboxylic acids include formic acid, acetic acid, propionic acid, heptanoic acid, octanoic acid, nonanoic acid, decanoic acid, benzoic acid, salicylic acid, and mixtures thereof.

Preferred two solvent antimicrobial compositions include peroxycarboxylic acid, fatty acid, iodophor, hypobromous acid, hypochlorous acid, an interhalide, a hypochlorite salt, a hypobromite salt, and/or peroxide as antimicrobial agent, preferably peroxycarboxylic acid, fatty acid, hypochlorous acid, and/or peroxide as antimicrobial agent, more preferably peroxycarboxylic acid or hypochlorous acid as antimicrobial agent.

The antimicrobial agent can be dissolved or dispersed in the second solvent or in the diluting solvent or can be selected to be more soluble in the first solvent or in the second solvent. Two solvent antimicrobial compositions of the invention containing antimicrobial agent typically have substantially greater antimicrobial effectiveness than comparison aqueous solutions or dispersions containing the antimicrobial agent alone. Although not limiting to the present invention, it is believed that this might arise due to partitioning of the antimicrobial agent preferentially into one of the solvents. Preferably, the antimicrobial agent is more soluble in or preferentially dissolves, disperses, or migrates into the second solvent compared to the diluting solvent. It is believed, without limiting the present invention, that an antimicrobial agent that is uncharged in the two solvent composition or that has more than 6 atoms including two carbon atoms will in part partition into the second solvent.

Typical two solvent antimicrobial compositions can include from about 0.001 wt-% to about 60 wt-% antimicrobial agent, preferably about 0.01 wt-% to about 15 wt-% antimicrobial agent, preferably about 0.08 wt-% to about 2.5 wt-% antimicrobial agent. Typical concentrate two solvent antimicrobial compositions can include from about 2.5 wt-% to about 25 wt-% antimicrobial agent. Typically, for use, two solvent antimicrobial compositions can include from about 0.001 wt-% to about 20 wt-% antimicrobial agent, preferably about 0.01 wt-% to about 10 wt-% antimicrobial agent, preferably about 0.08 wt-% to about 5 wt-% antimicrobial agent. Preferred two solvent antimicrobial compositions can include about 0.05, about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0 wt-% antimicrobial agent. These compositions can include the stated amounts or ranges not modified by about.

The level of reactive antimicrobial agent, such as peroxy acid, hydrogen peroxide, or halogen containing antimicrobial agent in a use composition can be affected, typically diminished, by organic matter that is found in or added to the use composition. Thus, the amounts of ingredients listed for the use compositions refer to the composition before or early in use, with the understanding that the amounts will diminish as organic matter is added to the use composition.

Peroxycarboxylic Acid Antimicrobial Agents

Two solvent antimicrobial compositions of the present invention can include as an antimicrobial agent a peroxycarboxylic acid and/or a carboxylic acid. Generally, carboxylic acids have the formula R—COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Preferably R is a small alkyl group with 1–10 carbons, most preferably 1–8 carbons.

Carboxylic acids which are generally useful are those having one or two carboxyl groups where the R group is a primary alkyl or aryl chain having a length of $C_2$ to $C_{12}$. The primary alkyl or aryl chain is that carbon chain of the molecule having the greatest length of carbon atoms and directly appending carboxyl functional groups. Examples of suitable carboxylic acids include acetic acid, propionic acid, hexanoic acid, heptanoic acid, octanoic acid, nonanoic acid, decanoic acid, benzoic acid, salicylic acid, and mixtures thereof. Longer chain carboxylic acid analogues, including hexanoic, heptanoic, octanoic, nonanoic, and decanoic, can be additionally antimicrobial and reduce surface tension to assist in wetting of hydrophobic surfaces.

Peroxycarboxylic (or percarboxylic) acids generally have the formula $R(CO_3H)_n$, where R is an alkyl, arylalkyl, cycloalkyl, carboxy alkyl, carboxyester alkyl, aromatic, or heterocyclic; and n is one, two, or three, and named by prefixing the parent acid with peroxy. While peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic and peroxysuberic acid and mixtures thereof.

Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids. In a preferred embodiment, the antimicrobial composition includes a peroxycarboxylic acid having 2 carbon atoms and another having from 7 to 12 carbon atoms. Preferably, such an antimicrobial composition includes peroxyacetic acid and peroxyoctanoic acid, peroxydecanoic acid, or mixtures thereof.

Typical two solvent antimicrobial compositions include $C_2$ to $C_{10}$ peroxy carboxylic acid. Preferred two solvent antimicrobial compositions include peroxyacetic acid, peroxyheptanoic acid, peroxyoctanoic acid, peroxypropionic acid, or mixtures thereof as peroxycarboxylic acid. Preferred two solvent antimicrobial compositions include peroxyacetic acid, peroxyheptanoic acid, peroxyoctanoic acid, or mixtures thereof as peroxycarboxylic acid.

The amount of peroxycarboxylic acid in use and concentrate compositions can range up to the limits at which the peroxycarboxylic acid can be dissolved or suspended in the composition. Preferably, the peroxycarboxylic acid is present in concentrate compositions at concentrations of from about 0.001 to about 50% by weight, preferably from 0.05 to about 25% by weight, preferably from about 0.08 to about 15% by weight, preferably from about 0.1 to about 10% by weight. In certain preferred embodiments the two solvent concentrate composition contains peroxycarboxylic acid at amounts at the lower end of these ranges. These compositions can include the stated amounts or ranges not modified by about.

Use compositions can be made, for example, by diluting a concentrate or by mixing individual ingredients at the point of use. Typically use solutions of the above concentrate compositions include, independently, peroxycarboxylic acid at concentrations of from 0.001 to about 5% by weight, preferably from 0.01 to about 3% by weight, and more preferably from about 0.1 to about 2% by weight. For example, use compositions of two solvent antimicrobial compositions can include from about 0.001 wt-% to about 5 wt-% peroxyacetic acid, preferably about 0.01 wt-% to about 2.5 wt-% peroxyacetic acid, preferably about 0.1 wt-% to about 1.5 wt-% peroxyacetic acid. For example, use compositions of two solvent antimicrobial compositions can include from about 0.001 wt-% to about 5 wt-% peroxyacetic acid and/or 0.0001 to about 3 wt-% peroxyoctanoic acid, preferably about 0.01 wt-% to about 2.5 wt-% peroxyacetic acid and/or 0.001 to about 1 wt-% peroxyoctanoic acid, preferably about 0.03 wt-% to about 0.5 wt-% peroxyacetic acid and/or peroxyoctanoic acid. These compositions can include the stated amounts or ranges not modified by about.

Ester Peroxycarboxylic Acid Antimicrobial Agents

As used herein, ester peroxycarboxylic acid refers to a molecule having the formula:

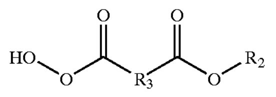

In this formula, $R_2$ and $R_3$ can independently be any of a wide variety of organic groups (e.g., alkyl, linear or cyclic, aromatic or saturated) or substituted organic groups (e.g., with one or more heteroatoms or organic groups). Ester peroxycarboxylic acid can be made using methods typically employed for producing peroxycarboxylic acid, such as incubating the corresponding monoester or diester dicarboxylate with hydrogen peroxide. Ester peroxycarboxylic acids derived from or corresponding to the diester dicarboxylates described herein are preferred.

Preferred ester peroxycarboxylic acids include alkyl ester peroxycarboxylic acids, preferably having the formula:

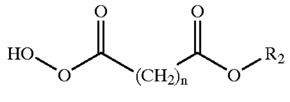

where $R_2$ represents an alkyl group having from 1 to 8 carbons and n is 0 to 8, preferably 2 to 6. The alkyl group can be either straight chain or branched. Preferably, $R_2$ is a methyl, ethyl, propyl (n-, iso-), butyl (n-, iso-, tert-), n-amyl, n-hexyl, or 2-ethylhexyl group. Preferably, n is 2, 3, 4, 5, or 6. In one preferred embodiment, the composition of the present invention includes a mixture of alkyl ester peroxycarboxylic acids in which n is 2, 3, and 4. Such a mixture includes monoesters of peroxyadipic, peroxyglutaric, and peroxysuccinic acids. In another preferred embodiment, a majority of the ester peroxycarboxylic acid in the composition has n equal to 3. In a preferred embodiment, $R_2$ is a $C_1$–$C_8$ alkyl. In a preferred embodiment, n is 1, 2, 3, or 4. Most preferably, $R_2$ is a $C_1$ alkyl, $C_2$ alkyl, $C_3$ alkyl, or $C_4$ alkyl, and n is 2, 3 or 4, or a combination thereof. In another most preferred embodiment, R2 is a $C_5$–$C_8$ alkyl, n is 5 or 6.

Alkyl ester peroxycarboxylic acids useful in this invention include all monoesters of monoperoxyoxalic acid, monoperoxymalonic acid, monoperoxysuccinic acid, monoperoxyglutaric acid, monoperoxyadipic acid, monoperoxypimelic acid, monoperoxysuberic acid, and monoperoxysebacic acid (or mixtures thereof) with methanol, ethanol, propanol (e.g., n-propanol or isopropanol), butanol (e.g., n-butanol, iso-butanol, or tert-butanol), amyl alcohol (e.g., n-pentanol, iso-pentanol, sec-pentanol, or tert-pentanol), hexanol (e.g., n-hexanol, iso-hexanol, sec-hexanol, or tert-hexanol), octanol (e.g., n-octanol, iso-octanol, sec-octanol, or tert-octanol) or mixtures thereof.

Such alkyl ester peroxycarboxylic acids include monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxypimelic acid, monomethyl monoperoxysuberic acid, monomethyl peroxysuberic acid, monomethyl monoperoxysebacic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid, monoethyl monoperoxypimelic acid, monoethyl monoperoxysuberic acid, monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxypimelic acid, monopropyl monoperoxysuberic acid, monopropyl monoperoxysebacic acid, in which propyl can be n- or iso-propyl; monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxypimelic acid, monobutyl monoperoxysuberic acid, monobutyl monoperoxysebacic acid, in which butyl can be n-, iso-, or t-butyl; monoamyl monoperoxyoxalic acid, monoamyl monoperoxymalonic acid, monoamyl monoperoxysuccinic acid, monoamyl monoperoxyglutaric acid, monoamyl monoperoxyadipic acid, monoamyl monoperoxypimelic acid, monoamyl monoperoxysuberic acid, monoamyl monoperoxysebacic acid, in which amyl is n-pentyl, iso-pentyl, sec-pentyl, or tert-pentyl; monohexyl monoperoxysebacic acid, in which hexyl is n-hexyl, isohexyl, sec-hexyl, or tert-hexyl; mono-2-ethylhexyl monoperoxysebacic acid.

Preferred alkyl ester peroxycarboxylic acids include monomethyl peroxyoxalic acid, monomethyl peroxymalonic acid, monomethyl peroxysuccinic acid, monomethyl peroxyglutaric acid, monomethyl peroxyadipic acid, monomethyl peroxypimelic acid, and monomethyl peroxysuberic acid.

The amount of ester peroxycarboxylic acid in use and concentrate compositions can range up to the limits at which the ester peroxycarboxylic acid can be dissolved or suspended in the composition. Preferably, the ester peroxycarboxylic acid is present in concentrate compositions at concentrations of from about 0.001 to about 50% by weight, preferably from 0.05 to about 25% by weight, preferably from about 0.08 to about 15% by weight, preferably from about 0.1 to about 10% by weight. In certain preferred embodiments the two solvent concentrate composition contains ester peroxycarboxylic acid at amounts at the lower end of these ranges. These compositions can include the stated amounts or ranges not modified by about.

Use compositions can be made, for example, by diluting a concentrate or by mixing individual ingredients at the point of use. Typically use solutions of the above concentrate compositions include, independently, ester peroxycarboxylic acid or alkyl ester peroxycarboxylic acid at concentrations of from 0.001 to about 5% by weight, preferably from 0.01 to about 3% by weight, and more preferably from about 0.1 to about 2% by weight.

Hydrogen Peroxide

The two solvent compositions of the invention typically also include a hydrogen peroxide constituent. Hydrogen peroxide in combination with the percarboxylic acid provides certain biofilm removal or antimicrobial action against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible.

Many oxidizing agents can be used for generating peroxycarboxylic acids. Suitable oxidizing agents, in addition to hydrogen peroxide, include inorganic and organic peroxides, such as, salts of perborate, percarbonate, and persulfate, percarbonic acid, and ozone. Hydrogen peroxide is generally preferred for several reasons. After application of the $H_2O_2$/peroxycarboxylic acid germicidal agent, the residue left merely includes water and an acidic constituent. Deposition of these products on the surface of a food product processing apparatus, such as a bath or spray apparatus, will not adversely effect the apparatus, the handling or processing, or the food product washed therein.

Typical two solvent antimicrobial compositions can include from about 0.005 wt-% to about 75 wt-% hydrogen peroxide, preferably about 0.01 wt-% to about 25 wt-% hydrogen peroxide, preferably about 0.05 wt-% to about 10 wt-% hydrogen peroxide, preferably about 0.1 wt-% to about 5 wt-% hydrogen peroxide. Use compositions of two solvent antimicrobial compositions can include from about 0.001 wt-% to about 5 wt-% hydrogen peroxide, preferably about 0.01 wt-% to about 2.5 wt-% hydrogen peroxide, most preferably about 0.1 wt-% to about 1.5 wt-% hydrogen peroxide.

Cosolvent

A variety of cosolvents can be employed. In general, the cosolvent is selected based, upon the characteristics of the chosen antimicrobial solvent and the solubility of the chosen antimicrobial solvent in the diluting solvent. For compositions in which water serves as the diluting solvent, the cosolvent generally will have higher water solubility than the water solubility of the chosen solvent. Preferably, the cosolvent has a high flashpoint (e.g., greater than about 30° C., more preferably greater than about 50° C., and most preferably greater than about 100° C.), low odor and low human and animal toxicity.

Preferred cosolvents include 2-(2-aminoethoxy)ethanol, monoethanolamine, diethanolamine, triethanolamine, amyl acetate, amyl alcohol, butanol, 3-butoxyethyl-2-propanol, butyl acetate, n-butyl propionate, cyclohexanone, diacetone alcohol, diethoxyethanol, diethylene glycol methyl ether, diethylene glycol n-butyl ether, diisobutyl carbinol, diisobutyl ketone, dimethyl heptanol, dipropylene glycol n-butyl ether, dipropylene glycol methyl ether, dipropylene glycol propyl ether, dipropylene glycol tert-butyl ether, ethanol, ethyl acetate, 2-ethylhexanol, ethyl propionate, ethylene glycol butyl ether, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol n-butyl ether, propylene glycol ethyl ether, propylene glycol methyl ether, propylene glycol n-propyl ether, tripropylene glycol methyl ether and tripropylene glycol n-butyl ether. Ethylene glycol butyl ether and dipropylene glycol n-butyl ether are particularly preferred cosolvents. Mixtures of cosolvents can be used if desired.

Commercially available cosolvents (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

A more preferred co-solvent would be compatible as an indirect or direct food additive or substance; especially those described in the Code of Federal Regulations (CFR), Title 21—Food and Drugs, parts 170 to 186 (which is incorporated herein by reference). Examples of such compatible cosolvents include glycerine, sorbitol, ethanol, propylene glycol, and the like.

Typical two solvent antimicrobial compositions can include up to about 45 wt-% cosolvent, preferably up to about 20 wt-% cosolvent, more preferably up to about 10 wt-% cosolvent, most preferably up to about 5 wt-% cosolvent. Use compositions of two solvent antimicrobial compositions typically include up to about 10 wt-% co-solvent, preferably up to about 5 wt-% cosolvent, preferably up to about 3 wt-% cosolvent. These compositions can include the stated amounts or ranges not modified by about. Preferred two solvent antimicrobial compositions include glycerine, ethanol, propylene glycol, sorbitol, or mixtures thereof, and the like as cosolvent. Preferred two solvent antimicrobial compositions include propylene glycol, glycerine, or mixtures thereof as cosolvent. Preferred two solvent antimicrobial compositions include propylene glycol as cosolvent.

Surfactant or Hydrotrope

A variety of surfactants or hydrotropes can be employed. In general, the surfactant identity and use level is selected based upon characteristics of the selected second solvent and other additives, such as its solubility in the diluting solvent (usually water or a densified fluid such as carbon dioxide). Preferably, the surfactant does not tend to cause formation of insoluble deposits, and has low odor and low toxicity. Mixtures of surfactants can be used if desired.

Suitable surfactants include nonionic surfactants, anionic surfactants, cationic surfactants, amphoteric surfactants, amine oxides, and the like. Preferred surfactants include anionic surfactants and amine oxides. Preferred surfactants which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and $C_8$–$C_{10}$ alkyl glucosides.

Other surfactants or hydrotropes for use in the present invention include n-octanesulfonate, available as NAS 8D from Ecolab, n-octyl dimethylamine oxide, n-decyl dimethyl amine oxide, cocoa dimethylamine oxide, and the commonly available aromatic sulfonates such as the alkyl benzene sulfonates (e.g., dodecylbenzene sulfonate, cumene sulfonate, xylene sulfonates) or naphthalene sulfonates.

The most preferred anionic surfactants and hydrotropes include C6–C24 alkylbenzene sulfonates; C6–C24 olefin sulfonates; C6–C24 paraffin sulfonates; cumene sulfonate; xylene sulfonate; C6–C24 alkyl naphthalene sulfonates; C6–C24 alkyl or dialkyl diphenyl ether sulfonates or disulfonates, C4–C24 mono or dialkyl sulfosuccinates; sulfonated or sulfated fatty acids; C6–C24 alcohol sulfates (preferably C6–C12 alcohol sulfates); C6–C24 alcohol ether sulfates having 1 to about 20 ethylene oxide groups; and C4–C24 alkyl, aryl or alkaryl phosphate esters or their alkoxylated analogues having 1 to about 40 ethylene, propylene or butylene oxide units or mixtures thereof.

Other surfactants include nonionic surfactants of C6–C24 alcohol ethoxylates (preferably C6–C14 alcohol ethoxylates) having 1 to about 20 ethylene oxide groups (preferably about 9 to about 20 ethylene oxide groups); C6–C24 alkylphenol ethoxylates (preferably C8–C10 alkylphenol ethoxylates) having 1 to about 100 ethylene oxide groups (preferably about 12 to about 20 ethylene oxide groups); ethylene oxide/propylene oxide/butylene oxide copolymers having 1 to about 400 ethylene oxide groups and 2 to about 100 propylene oxide groups and up to about 40 butylene oxide groups (either as block, heteric, or random mixed order); C6–C24 alkylpolyglycosides (preferably C6–C20 alkylpolyglycosides) having 1 to about 20 glycoside groups (preferably about 9 to about 20 glycoside groups); C6–C24 fatty acid ester ethoxylates, propoxylates or glycerides; and C4–C24 mono or dialkanolamides. A particularly useful nonionic surfactant for use as a defoamer is nonylphenol having an average of 12 moles of ethylene oxide condensed thereon, it being end capped with a hydrophobic portion including an average of 30 moles of propylene oxide.

More preferred surfactants include food grade surfactants, linear alkylbenzene sulfonic acids and their salts, and ethylene oxide/propylene oxide derivatives sold under the Pluronic™ trade name.

Preferred cationic surfactants include quaternary ammonium compounds having the formula:

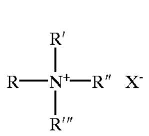

where R, R', R" and R'" are each a $C_1$–$C_{24}$ alkyl, aryl or aralkyl group that can optionally contain one or more P, O, S or N heteroatoms, and X is F, Cl, Br, I or an alkyl sulfate. Additional preferred cationic surfactants include ethoxylated and/or propoxlyated alkyl amines, diamines, or triamines.

Preferred amphoteric surfactants include amine oxide compounds having the formula:

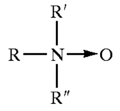

where R, R', R" and R'" are each a $C_1$–$C_{24}$ alkyl, aryl or aralkyl group that can optionally contain one or more P, O, S or N heteroatoms.

Another class of preferred amphoteric surfactants includes betaine compounds having the formula:

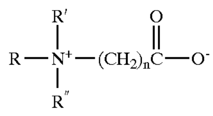

where R, R', R" and R'" are each a $C_1$–$C_{24}$ alkyl, aryl or aralkyl group that can optionally contain one or more P, O, S or N heteroatoms, and n is about 1 to about 10.

A most preferred surfactant would be compatible as an indirect or direct food additive or substance; especially those described in the Code of Federal Regulations (CFR), Title 21—Food and Drugs, parts 170 to 186 (which is incorporated herein by reference).

Typical two solvent antimicrobial compositions can include up to about 45 wt-% surfactant and/or hydrotrope, preferably up to about 20 wt-% surfactant and/or hydrotrope, preferably up to about 10 wt-% surfactant and hydrotrope, preferably up to about 5 wt-% surfactant and hydrotrope. Use compositions of the two solvent antimicrobial compositions can include up to about 10 wt-% surfactant and hydrotrope, preferably up to about 5 wt-% surfactant and hydrotrope, more preferably up to about 3 wt-% surfactant and hydrotrope.

Adjuvants

The two solvent composition of or employed in the method of the invention can also include any number of adjuvants. Specifically, the composition can include stabilizing agents, wetting agents, hydrotropes, thickeners, foaming agents, chelating agents, builders, pH adjusters, anticorrosion additives, antirust additives indicators as well as fragrances, pigments, or dyes among any number of constituents which can be added to the composition. Such adjuvants can be preformulated with the two solvent composition or added to the system simultaneously, or even after, the addition of the two solvent composition. The composition can also contain any number of other constituents as necessitated by the application, which are known and which can facilitate the activity of the present invention.

Stabilizing Agents

The present two-solvent antimicrobial compositions can include components such as stabilizing agents, particularly those suitable for stabilizing peroxygen compounds or peroxycarboxylic acids. Such stabilizers are well-known. Such stabilizers include organic chelating compounds that sequester metal ions in solution, particularly most transition metal ions, which would promote decomposition of any peroxygen compounds therein. Typical complexing agents include organic amino- or hydroxy-polyphosphonic acid complexing agents (either in acid or soluble salt forms), carboxylic acids, hydroxycarboxylic acids, or aminocarboxylic acids.

Chelating agents or sequestrants generally useful as stabilizing agents in the present compositions include salts or acids of (expressed in acid form) dipicolinic acid, picolinic acid, gluconic acid, quinolinic acid, and alkyl diamine polyacetic acid-type chelating agents such as ethylenediamine tetraacetic acid (EDTA), hydroxyethylethylethylene diamine triacetic acid (HEDTA), and ethylene triaminepentaacetic acid, acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylenephosphonic acid)]; 2-phosphene butane-1,2,4-tricarboxylic acid; as well as the alkyl metal salts, ammonium salts, or alkyloyl amine salts, such as mono, di, or tetra-ethanolamine salts.

The stabilizing agent can be used in a concentrate at a concentration typically ranging from about 0 wt-% to about 20 wt-% of the composition, preferably from about 0.1 wt-% to about 10 wt-% of the composition, and most preferably from about 0.2 wt-% to 5 wt-% of the composition. In a use solution they range from 0 wt-% to about 5 wt-% of the composition, preferably from 0 wt-% to about 2 wt-% of the composition, and most preferably from 0 wt-% to 0.5 wt-% of the composition Amino phosphates and phosphonates are also suitable for use as chelating agents in the compositions and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2–4 carboxylic acid moieties and about 1–3 phosphonic acid groups. Such acids include 1-phosphono-1-methylsuccinic acid, phosphonosuccinic acid and 2-phosphonobutane-1,2,4-tricarboxylic acid.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in a concentrate of the present invention generally ranges up to about 10 wt-%, preferably up to about 2 wt-%, more preferably up to about 0.5 wt-%. In a use solution they can typically range up to about 5 wt-% of the composition, preferably up to about 1 wt-% of the composition, and most preferably up to 0.5 wt-% of the composition.

Buffering Agents

Buffering agents can be added to the composition, for example, to stabilize the pH of an antimicrobial solution. While generally free of strong acids, the two solvent compositions of the invention might include buffering adjuvants such as weak inorganic acids, organic acids, organic salts, and inorganic salts for buffering purposes. These might include an inorganic-based salt or weak inorganic acids including phosphates (including mono-, di-, or tri-basic potassium, calcium, or sodium phosphate), sulfates (including sodium, potassium, and magnesium sulfates), bisulfates, silicates (including sodium, potassium, and magnesium silicates), borates (including sodium or potassium borates, and boric acid), sulfamic acid; organic-based compounds such as malic acid, tartaric acid, citric acid, acetic acid, glycolic, glutamic acid, sorbic acid, benzoic acid, adipic acid, succinic acid, diacetate salts, or dimer and fatty acids; or mixtures thereof.

Additionally, carbonation acidification via the interaction of carbon dioxide with water is possible for aqueous formulations.

Some additional acids or salts that may be optionally added to the present invention for pH control, buffering, include aliphatic or olefinic carboxylic acids or carboxylate salts, aromatic carboxylic acids or carboxylic salts, inorganic acids or salts, polymeric carboxylic acids or carboxylate salts, organic-phosphonates, organic-phosphates or their salts, organic-sulfonates, organic-sulfates or their salts, organic boric acids or salts, amino acids or salts, or mixtures thereof. Most preferably the invention could include carboxylic acids, di/tri-carboxylic acids, hydroxy carboxylic acids, or alpha-hydroxy carboxylic acids—or their salts, anhydride, or esters—such as glycolic, lactic, malic, citric, tartaric, acetic, diacetate, butyric, octanoic, heptanoic, nonanoic, decanoic, malonic, adipic, succinic, salicylic, fumaric, maleic, acetoacetic, oxalacetic, pyruvic, $\alpha$-ketoglutaric, and so forth. Preferably mild acids are used in the present invention.

Most preferred acid/salt combinations for use as buffers in the present invention include citric/citrate, phosphoric/phosphate, boric/borate, sulfuric/bisulfate, succinic/succinate buffer, or mixtures thereof, or any of these acids with any of the salts. The acid or buffer are, however, optional to the present two solvent compositions.

Formulating Two Solvent Antimicrobial Compositions

The two solvent antimicrobial compositions of the invention can be formulated to include the diluting solvent (e.g., water) as sold, or the diluting solvent can be added at any time up to the time of use. Preferably, the concentrates of the invention contain little or no diluting solvent as sold. A variety of dilution ratios can be employed, so long as the diluted composition exhibits the desired antimicrobial behavior when applied to the target microbes.

The ingredients in the concentrate can represent about 0.01 to about 99 wt-% of the diluted mixture, more preferably about 0.1 to about 50 wt-%, and most preferably about 0.5 to about 25 wt-%. The diluted antimicrobial compositions preferably contain about 0.01 to about 50 wt-% of the second solvent, with concentrations of about 0.1 to 10 wt-% being more preferred and concentrations of about 0.5 to about 5 wt-% being most preferred. As a further guide, the diluted composition preferably contains antimicrobial solvent in an amount near the solubility limit of the antimicrobial solvent in the diluting solvent. In addition, the diluted antimicrobial compositions preferably are aqueous, contain antimicrobial agent, and are clear.

The compositions of the invention can be sold in the form of a kit containing the composition together with suitable directions for carrying out the method of the invention. Such directions typically will include recommended dilution ratios, applications, application techniques and safety warnings.

Methods Employing the Two Solvent Compositions

The two solvent antimicrobial compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices, pharmaceutical plants or co-packers, and food plants or co-packers, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin.

The two solvent antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps and pre- or post-surgical scrubs.

The two solvent antimicrobial compositions can also be used in veterinary products such as mammalian skin treatments (e.g. a teat dip) or in products for sanitizing or disinfecting animal enclosures, pens, watering stations, and veterinary treatment areas such as inspection tables and operation rooms.

The present two solvent compositions can be employed for reducing the population of pathogenic microorganisms, such as pathogens of humans, animals, and the like. The two solvent compositions can exhibit activity against pathogens including fungi, molds, bacteria, spores, and viruses, for example, parvovirus, coxsackie virus, herpes virus, *S. aureus, E. coli, Streptococci, Legionella*, mycobacteria, or the like. Such pathogens can cause a varieties of diseases and disorders, including athletes foot, hairy hoof wart disease, Mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The two solvent antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The present two solvent compositions are useful in the cleaning or sanitizing of containers, processing facilities, or equipment in the food service, food processing, beverage, dairy, brewery, and pharmaceutical industries. The antimicrobial compositions have particular value for use on food, beverage, and pharmaceutical packaging materials and equipment, and especially for cold or hot aseptic packaging. Examples of process facilities in which the composition of the invention can be employed include a milk line dairy, a continuous brewing system, food processing lines such as pumpable food systems and beverage lines, pharmaceutical fill lines or tabletizers and bottlers, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET, various copolymers, bottles of various volumes (100 ml to 2 liter, etc.), one gallon milk containers, aluminum foil, paper board juice or milk containers, etc. A detailed description of additional treatable food, beverage, and pharmaceutical packaging container materials are found in the Code of Federal Regulations, Title 21, parts 175 to 178.

The antimicrobial compositions can also be used on or in other industrial equipment and in other industrial process streams such as heaters, cooling towers, boilers, retort waters, rinse waters, aseptic packaging wash waters for foods, pharmaceuticals, and beverages, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella.*

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant sanitizing composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, more preferably about 30 to about 120 seconds. The present sanitizing composition is found to remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities includes the following steps. The use composition of the invention is introduced into the process facilities at a temperature in the range of about 4° C. to 80° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition is preferably circulated through the process facilities for 10 minutes or less.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use composition is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with a two solvent composition of the invention. Contacting can include any of numerous methods for applying a composition, such as spraying the composition, immersing or flooding the object in or with the composition, foam or gel treating the object with the composition, fogging, atomizing, or aerosolizing, annular misting, or a combination thereof.

A concentrate or use concentration of a two solvent composition of the present invention can be applied to or brought into contact with an object by any conventional method or apparatus for applying an antimicrobial or cleaning composition to an object. For example, the object can be wiped with, sprayed with, and/or immersed in the two solvent composition, or a use composition made from the two solvent composition. The two solvent composition can be sprayed or wiped onto a surface; the composition can be caused to flow over the surface, or the surface can be dipped into the composition. Contacting can be manual or by machine.

The compositions can be formulated as liquids, gels, aerosols, waxes, solids, or powders. If steam or another gaseous diluting solvent is employed, then the compositions can be formulated to be applied in a gaseous state.

Methods for Beverage, Food, and Pharmaceutical Processing

The two solvent antimicrobial compositions of the invention can be used in the manufacture of beverage, food, and pharmaceutical materials including fruit juice, dairy products, malt beverages, soybean-based products, yogurts, baby foods, bottled water products, teas, cough medicines, drugs, and soft drinks. The materials can be used to sanitize, disinfect, act as a sporicide for, or sterilize bottles, pumps, lines, tanks and mixing equipment used in the manufacture of such beverages. Further, the two solvent antimicrobial compositions can be used in aseptic, cold filling operations in which the interior of the food, beverage, or pharmaceutical container is sanitized or sterilized prior to filling. In such operations, a container is contacted with the sanitizing two solvent composition material, typically using a spray, or dipping, or filling device to intimately contact the inside of then container with the two solvent composition, for sufficient period of time to reduce microorganism populations within the container. The container is then emptied of the amount of sanitizer or sterilant used. After emptying, the container can then be commonly rinsed with potable water or sterilized water and again emptied; however, this is not a required step of the current invention. After rinsing, the container is then filled with the beverage, food, or pharmaceutical. The container is then sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacterial of the genus *Bacillus spp.* can be a significant problem in bottling processes, particularly in cold aseptic bottling processes. The two solvent sanitizer materials of the invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the two solvent materials of the invention can be used to sanitize the interior of beverage containers prior to filling with the carbonated beverage. Typical carbonated beverages in this application include cola beverage, fruit beverages, ginger ale beverages, root beer beverages, iced tea beverages which may be non-carbonated, and other common beverages considered soft drinks. The two solvent materials of the invention can be used to sanitize both the tanks, lines, pumps, and other equipment used for the manufacture and storage of the soft drink material and also used in the bottling or containers for the beverages. The two solvent sanitizing materials are useful for killing both bacterial and fungal microorganisms that can be present on the surfaces of the production equipment and beverage containers.

The present invention is based upon the surprising discovery that two solvent compositions can effectively kill microorganisms (e.g., >1 $\log_{10}$ and especially a 5 $\log_{10}$ reduction in 30 seconds) from a concentration level of at least about 50 part per million (ppm), preferably about 500 ppm, and most preferably about 1500 ppm of two solvent composition. Typically the two solvent composition, excluding water, would be present at a concentration of 0.01 to about 50 wt-%, preferably 0.1 to about 10 wt-%, and most preferably 0.5 to about 5 wt-%.

The FIGURE shows a schematic for an embodiment of a bottle spraying/bottling operation using two solvent composition including a cold aseptic operation. In the FIGURE, a plant 100 that can contact beverage bottles with a two solvent composition for a sanitizing regime is shown. In the FIGURE, bottles 110 are passed through a sterilizing tunnel 102. The sanitized bottles 110*a* then pass through a rinsing tunnel 103 and emerge as sanitized rinsed bottles 110*b*.

In the process, bulk two solvent composition is added to a holding tank 101. Commonly, the materials are maintained at a temperature of about 22° C. in tank 101. To obtain the effective use concentration of the two solvent composition, make-up water 105 is combined with the concentrated two solvent composition into the tank 101. The two solvent use composition is passed through a heater 108 to reach a temperature of about 45–50° C. The heated two solvent use composition is sprayed within sterilizing tunnel 102 into and onto all surfaces of the bottle 110. An intimate contact between the two solvent composition and the bottle 110 is essential for reducing microbial populations to a sanitizing level.

After contact with the two solvent use composition and after dumping any excess composition from the bottles, the sanitized bottles 110 are then passed to a fresh water rinse tunnel 103. Fresh water 108 is provided from a fresh water make-up into a spray rinsing tunnel 103. Excess spray drains from rinsing tunnel 103 to drain 106. Within the tunnel 103, sanitized bottles 110*a* are thoroughly rinsed with fresh water. The complete removal of the two solvent composition from the bottles 110*a* is important for maintaining high quality of the beverage product. The rinsed and sanitized bottles 110*b* are then removed from the rinsing tunnel.

The day tank 101, the sterilizing tunnel 102 and the rinsing tunnel 103 are all respectively vended to wet scrubber or vent 111*a*, 111*b* or 111*c* to remove vapor or fumes from the system components. The sanitizer material that has been sprayed and drained from the bottles 110*a* accumulate in the bottom of the spray tunnel 102 and is then recycled through recycle line and heater 107 into the day tank 101.

The day tank is used for diluting, storing, and delivering the two solvent use composition which can include 0.01 to about 50 wt-%, preferably 0.1 to about 10 wt-%, and most preferably 0.5 to about 5 wt-% two solvent composition. All active treating equipment should be vented to a wet scrubber to prevent fumes from entering the atmosphere from the treatment equipment. Draining of the containers of their two solvent composition is important to reduce carry over minimized product loss. The contact between the bottles and the two solvent antimicrobial composition is typically at a temperature of greater than about 0° C., more typically greater than 25° C., and most typically greater than about 40° C. Often temperatures between about 40° C. and 90° C. are used. To obtain sanitization or sterilization of beverage containers at about 200 ppm to about 10,000 ppm, more preferably 500 ppm to about 5,000 ppm, and most preferably 700 ppm to about 2,500 ppm two solvent composition, contact at 40° C. to 60° C. for at least 5 sec, more preferably 10 sec, contact time is required.

Sanitizing or sterilizing conditions are greatly dependent on the processing temperatures, times, soil loading, water quality, and the like. Preferably, the sanitization equipment, day tank, sanitizing tunnel and rinsing tunnel are manufactured from polyolefin structural plastics, passivated stainless steel, or other non-corrosion sensitive production materials.

In the cold aseptic filling of 16 ounce polyethylene terephthalate (PET bottle), or other polymeric, beverage containers, a process has been adopted using a two solvent composition, The two solvent composition is diluted to a use concentration of about 0.1 to about 10 wt % and is maintained at an effective elevated temperature of about 25° C. to about 70° C., preferably about 40° C. to about 60° C. The spray or flood of the bottle with the material ensures contact between the bottle and the sanitizer material for at least 5, preferably 10, seconds. After flooding is complete, the bottle is drained of all contents for a minimum of 2 seconds and optionally followed by a 5 second water rinse with sterilized water using about 200 milliliters of water at 38° C. (100° F.). If optionally filled with the rinse water, the bottle is then drained of the sterilized water rinse for at least 2 seconds and is immediately filled with liquid beverage. After the rinse is complete, the bottles usually maintain less than 10, preferably 3, milliliters of rinse water after draining.

Methods for Contacting a Food Product

The present method and system provide for contacting a food product with a two solvent composition employing any method or apparatus suitable for applying a two solvent composition. For example, the method and system of the invention can contact the food product with a spray of a two solvent composition, by immersion in the two solvent composition, by foam or gel treating with the two solvent composition, or the like. Contact with a spray, a foam, a gel, or by immersion can be accomplished by a variety of methods known for applying antimicrobial agents to food. These same methods can also be adapted to apply the two solvent compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. Preferably the exposure time is at least about 5 to about 15 seconds.

A preferred method for washing food product employs a pressure spray including the two solvent composition. During application of the spray solution on the food product, the surface of the food product can be moved with mechanical action, preferably agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., preferably about 20 to 60° C. to increase efficacy. The spray two solvent composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One preferred automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the two solvent compositions of the invention. These steam jets can be used in combination with cooling water to ensure that the treatment reaching the food product surface is less than 65° C., preferably less than 60° C. The temperature of the spray on the food product is important to ensure that the food product is not substantially altered (cooked) by the temperature of the spray. The spray pattern can be virtually any useful spray pattern.

Immersing a food product in a liquid two solvent composition can be accomplished by any of a variety of known methods. For example, the food product can be placed into a tank or bath containing the two solvent composition. Alternatively, the food product can be transported or processed in a flume of the two solvent composition. The washing solution is preferably agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the two solvent composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2 wt-%. At time of use, compressed air can be injected into the mixture, then applied to the food product surface through a foam application device such as a tank foamer or an aspirated wall mounted foamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

The present invention may be better understood with reference to the following examples. These examples are intended to be representative of specific embodiments of the invention, and are not intended as limiting the scope of the invention.

EXAMPLES

The Examples that follow refer to several peroxycarboxylic acid compositions by tradenames or other designations. These proprietary compositions have formulations that can be described by the following mixes or that are at equilibria derived from the following mixes:

| Peracid Example Formulations | | | | | | |
|---|---|---|---|---|---|---|
| Ingredient | Mix 1 wt-% | Mix 2 wt-% | Mix 3 wt-% | Mix 4 wt-% | Mix 5 wt-% | Mix 6 wt-% |
| H2O2 (35%) | 21 | 51 | 85 | 26 | 25 | 50 |
| Acetic acid | 78 | 44 | 11 | 30 | 55 | 34 |
| HEDP | 1 | 1.5 | 1.5 | 1.5 | 0.5 | 0.1 |
| Water | | remainder | 2 | 26 | remainder | |
| C7 fatty acid | | 0 | 0 | 0 | 0 | 0.4 |
| C8 fatty acid | | 0 | 0 | 4 | 0 | |
| NAS | | 0 | 0 | 12.5 | 0 | 15.5 |

Example 1

Several compositions were evaluated by comparing them against a commercially available aseptic bottle washing biocide based on mixed peracids (MATRIXX™; Ecolab). Compositions containing only 1000 ppm or 2000 ppm of a single peracid or mixed peracids were used as controls. The remaining compositions were prepared by adding 10% of various solvents to an aqueous solution containing 1000 ppm or 2000 ppm of the mixed peracids. Non-solubilizing amounts of anionic surfactants were added to some of the compositions to affect minimal coupling and to yield, in some cases, pseudo-stable behavior and at least a partial phase-splitting condition. Addition of such non-stabilizing amounts tended to provide partial coupling and improved antimicrobial solution stability but not necessarily improved microbial control.

The compositions and controls were evaluated for antimicrobial activity using the procedure set out in set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2), using a 10 second contact time at 60° C. against the mold *Chaetomium funicola* (*C. funicola*). This brief contact time presented an especially challenging test, as evidenced by low observed log order reduction values for the controls.

Set out below in Table I are the run number, solvent, solvent description (in terms of its water solubility), peracid concentration, anionic surfactant concentration, appearance of the mixtures, after they had been allowed to stand for one minute, and observed log order reduction for *C. funicola*. The solvent description classified the solvents as highly soluble (>60% solubility in water), partially soluble (~20–60%), or sparingly soluble (<20%).

that the addition of partially soluble and sparingly soluble solvents provided a substantial improvement in the antimicrobial efficacy of a commercial aseptic wash product, as can be seen by comparing control Run Nos. 1-1 through 1-3 to Run Nos. 1-6 through 1-11. The improved performance of Run Nos. 1-8 through 1-11 was especially dramatic, in that the observed activity improvement was 5 or more orders of magnitude compared to control Run Nos. 1-1 through 1-3. Use of highly soluble solvents (Run Nos. 1-4 and 1-5) provided only a small improvement in antimicrobial efficacy.

Example 2

Several two solvent antimicrobial compositions including diluting solvent and a solvent only partially or sparingly soluble in that solvent were evaluated for biocidal control, using the method of Example 1, and compared to several commercial products and to formulations from several U.S. patents. The compositions of commercial products formed clear (single-phase) formulations when prepared according to instructions. The two solvent antimicrobial compositions including diluting solvent and a solvent only partially or sparingly soluble in that solvent formed pseudo-stable cloudy compositions that underwent phase splitting following application. All tested compositions were evaluated against the spore-forming, enterotoxin producing pathogens *Bacillus cereus* and *Bacillus subtilis* and the mold *C. funicola* using a 10 second contact time at 60° C.

TABLE I

| Run No. | Solvent | Solvent Description | Peracid Concentration | Anionic Surfactant Concentration | Appearance | *C. funicola* Log Reduction |
|---|---|---|---|---|---|---|
| 1-1 | None | None | 2000 ppm[1] | 0.0% | clear | 0.1 |
| 1-2 | None | None | 1000 ppm[2] | 0.26% | clear | 0.05 |
| 1-3 | None | None | 2000 ppm[2] | 0.52% | clear | 0.1 |
| 1-4 | Glycolic acid | highly soluble | 2000 ppm[2] | 0.62% | clear | 0.2 |
| 1-5 | Dimethyl sulfoxide | highly soluble | 2000 ppm[2] | 0.62% | clear | 0.3 |
| 1-6 | Hydrocarbon diol[3] | partially soluble | 2000 ppm[2] | 0.62% | slightly cloudy | 0.4 |
| 1-7 | Propylene carbonate | partially soluble | 2000 ppm[2] | 0.62% | slightly cloudy | 1.6 |
| 1-8 | Diester blend[4] | sparingly soluble | 2000 ppm[2] | 0.62% | very cloudy | 6.0 |
| 1-9 | Diester blend[4] | sparingly soluble | 2000 ppm[1] | 0.0% | very cloudy | >4.4 |
| 1-10 | Benzyl alcohol | sparingly soluble | 2000 ppm[2] | 0.62% | very cloudy | 5.0 |
| 1-11 | Benzyl alcohol | sparingly soluble | 2000 ppm[1] | 0.0% | very cloudy | >4.7 |

[1]Peracetic acid from TSUNAMI ™ 100 (Ecolab)
[2]Peracid from MATRIXX ™, a commercial peracid (Ecolab)
[3]VARONIC ™ TD-1 (Goldschmidt Chemical)
[4]DBE ™ (Dupont Nylon)

The compositions containing partially soluble solvents (Run Nos. 1-6 and 1-7) exhibited some phase-splitting behavior. The compositions containing sparingly soluble solvents (Run Nos. 1-8 through 1-11) exhibited substantial phase-splitting behavior. The results in Table I demonstrate Set out below in Table II are the run number, benzyl alcohol amount, amounts of additional ingredients, appearance of the mixtures, after they had been allowed to stand for one minute, and observed log order reduction for *B. cereus, Bacillus subtilis* and *C. funicola* for each composition.

TABLE II

| Run No. | Benzyl Alcohol Amount | Additional Ingredient Amounts[1] | Appearance | *B. cereus* Log Reduction | *B. subtilis* Log Reduction | *C. funicola* Log Reduction |
|---|---|---|---|---|---|---|
| 2-1 | 5.0% | DBS[2] (0.1%) | clear (1-phase) | 0.2 | 0.0 | >4.4 |
| 2-2 | 2.0% | DBS[2] (0.1%) | clear (1-phase) | 0.1 | — | >4.4 |
| 2-3 | 2.0% | DBS[2] (5.0%) | clear (1-phase) | 0.0 | 0.2 | 0.3 |
| 2-4 | 2.0% | Nonionic surfactant[3] (5.0%) | clear (1-phase) | 0.0 | 0.1 | 0.4 |
| 2-5 | 0.0% | BUTYL CELLOSOLVE ™ (10.0%), DBS[2] (2.4%), anhydrous sodium metasilicate (2.0%)[4] | clear (1-phase) | 0.0 | 0.2 | 3.2 |

TABLE II-continued

| Run No. | Benzyl Alcohol Amount | Additional Ingredient Amounts[1] | Appearance | *B. cereus* Log Reduction | *B. subtilis* Log Reduction | *C. funicola* Log Reduction |
|---|---|---|---|---|---|---|
| 2-6 | 6.0% | DBS[2] (1.3%), ammonium hydroxide 28% (0.2%), Na-octane-1-sulfonate 40% (1.0%),[5] | clear (1-phase) | 0.0 | 0.1 | >4.8 |
| 2-7 | 4.0% | Ethanol (10%)[6] | clear (1-phase) | 0.05 | 0.1 | 4.6 |
| 2-8 | 2.0% | Ethanol (10%)[7] | clear (1-phase) | 0.1 | — | 4.7 |
| 2-9 | 4.0% | Glycerine (10%), DBS (2%) + other chemicals[8] | clear (1-phase) | 0.1 | 0.0 | 4.7 |
| 2-10 | 4.0% | Peracid[9] (0.1%), NAS[10] (0.24%) | cloudy (2-phase) | >6.3 | — | >4.4 |
| 2-11 | 3.5% | Peracid[11] (0.15%) | cloudy (2-phase) | >6.3 | — | >4.5 |
| 2-12 | 3.0% | Peracid[12] (0.1%), NAS[10] (0.24%) | cloudy (2-phase) | >6.3 | >6.7 | 3.8 |
| 2-13 | 3.0% | Peracid[9] (0.1%), NAS[10] (0.24%) | cloudy (2-phase) | >6.5 | >6.7 | 4.0 |
| 2-14 | 3.0% | Peracid[13] (0.1%) | cloudy (2-phase) | >6.2 | — | 3.4 |
| 2-15 | 0.0% | Diester blend[14] (5%), peracid[11] (0.1%), LAS (0.1%) | cloudy (2-phase) | 5.0 | — | >4.4 |
| 2-16 | 0.0% | Diester blend[14] (5%), $H_2O_2$ (2.1%)[15] | cloudy (2-phase) | — | 2.9 | >4.4 |
| 2-17 | 0.0% | Diester blend[14] (5%), $H_2O_2$ (2.1%)[15] | cloudy (2-phase) | — | >6.0 | >4.4 |
| 2-18 | 0.0% | Diester blend[14] (5%), NaOCl (0.02%)[16] | cloudy (2-phase) | 6.0 | >6.1 | >4.8 |
| 2-19 | 5.0% | NaOCl (0.02%)[16] | cloudy (2-phase) | — | — | >4.8 |
| 2-20 | 0.0% | Diester blend[14] (2.5%), NaOCl (0.025%)[17] | clear (1-phase) | >6.0 | >6.1 | >3.4 |

[1]The remainder of these compositions contained water
[2]DBS = dodecylbenzene sulfonate
[3]TERGITOL ™ 15-S-9 (Union Carbide)
[4]See Example 25 of U.S. Pat. No. 5,158,710
[5]See Example 10 of U.S. Pat. No. 5,849,682
[6]See Example 4 of U.S. Pat. No. 5,180,749
[7]See Example 1 of U.S. Pat. No. 5,180,749
[8]See Example 3 of U.S. Pat. No. 5,635,492, made with 0.1% "Rhamsan gum," 1% phosphate buffer and 0.003% blue dye
[9]VORTEXX ™ or MATRIXX ™ commercial peracids (Ecolab)
[10]NAS = sodium, 1-octane sulfonate
[11]KX-6091 commercial peracid (Ecolab)
[12]15C commercial peracid (Ecolab)
[13]TSUNAMI-100 ™ commercial peracid (Ecolab)
[14]DBE-3 ™ (Dupont Nylon)
[15]Aged > 18 hours
[16]Acidified to pH = 5.0 with acetic acid
[17]Acidified to pH = 6.0 with acetic acid Except as otherwise noted, the comparative compositions in Run Nos. 2-1 through 2-9 were prepared according to the listed examples of the cited patents or according to the mixing instructions of the cited commercial products. Each was found to yield a non-phase-splitting formulation. The compositions in Run Nos. 2-10 through 2-19 yielded phase-splitting formulations that formed at least 2 phases. Run No. 2-20 yielded a pseudo-stable solution that was just slightly opaque but did not separate during the test time.

The two solvent antimicrobial compositions including diluting solvent and a solvent only partially or sparingly soluble in that solvent exhibited significant antimicrobial efficacy against *B. cereus*, as well as broad-spectrum efficacy against *B. subtilis* and *C. funicola*. However, the composition of Run No. 2-19 underwent a chemical reaction and could not be employed at the desired active level against the *Bacillus* spores.

Example 3

Using the method of Example 1, 5% portions of various sparingly soluble solvents were added to plain water or to commercial peracid bottle washing formulas (KX-6091, 15C, or VORTEXX™; Ecolab) and tested against the mold *C. funicola* using a 10 second contact time at 60° C. A non-emulsifying amount of the anionic surfactant sodium octene sulfonate was added to some of the compositions to slow down, but not prevent, phase-splitting.

Set out below in Table III are the run number, solvent, peracid, peracid concentration, surfactant concentration, appearance of the mixtures after they had been allowed to stand for 1 minute, and observed log order reduction for *C. funicola* for each composition.

TABLE III

| Run No. | Solvent | Peracid | Peracid Concentration | Surfactant Concentration | Appearance | *C. funicola* Log Reduction |
|---|---|---|---|---|---|---|
| 3-1 | None | KX-6091[1] | 2000 ppm | 0 ppm | clear (1-phase) | 0.2 |
| 3-2 | None | 15C[1] | 2000 ppm | 2500 ppm | clear (1-phase) | 0.2 |
| 3-3 | None | VORTEXX[1] | 2000 ppm | 5960 ppm | clear (1-phase) | 0.1 |
| 3-4 | Glycol solvents[2] | KX-6091[1] | 2000 ppm | 0 ppm | cloudy (2-phase) | 1.3 |
| 3-5 | Glycol solvents[3] | KX-6091[1] | 2000 ppm | 0 ppm | cloudy (2-phase) | 3.7 |
| 3-6 | Glycol solvents[4] | KX-6091[1] | 2000 ppm | 0 ppm | cloudy (2-phase) | 3.2 |
| 3-7 | Diester blend[5] | KX-6091[1] | 2000 ppm | 1000 ppm[7] | cloudy (2-phase) | >4.4 |
| 3-8 | Glycol solvents[6] | None | 0 ppm | 1000 ppm[7] | cloudy (2-phase) | 2.8 |
| 3-9 | Glycol solvents[6] | KX-6091[1] | 1000 ppm | 1000 ppm[7] | cloudy (2-phase) | 4.3 |

TABLE III-continued

| Run No. | Solvent | Peracid | Peracid Concentration | Surfactant Concentration | Appearance | *C. funicola* Log Reduction |
|---|---|---|---|---|---|---|
| 3-10 | Glycol solvents[6] | KX-6091[1] | 2000 ppm | 1000 ppm[7] | cloudy (2-phase) | >4.4 |
| 3-11 | 2-ethyl-1-hexanol | KX-6091[1] | 2000 ppm | 1000 ppm[7] | cloudy (2-phase) | >4.2 |
| 3-12 | Dipentene | KX-6091[1] | 2000 ppm | 1000 ppm[7] | cloudy (2-phase) | 2.7 |
| 3-13 | Amyl acetate | KX-6091[1] | 2000 ppm | 1000 ppm[7] | cloudy (2-phase) | 3.3 |
| 3-14 | Benzyl alcohol | None | 0 ppm | 0 ppm | cloudy (2-phase) | >4.2 |
| 3-15 | Benzyl alcohol | KX-6091[1] | 2000 ppm | 0 ppm | cloudy (2-phase) | >4.2 |
| 3-16 | Tetrabutyl ammonium hydroxide[7] | 15C[1] | 2000 ppm | 2500 ppm | cloudy (2-phase) | 1.7 |
| 3-17 | Phenoxyethanol | 15C[1] | 2000 ppm | 2500 ppm | cloudy (2-phase) | 3.9 |
| 3-18 | Phenoxyethanol | VORTEXX[1] | 2000 ppm | 5960 ppm | cloudy (2-phase) | 4.8 |

[1]Commercial peracid (Ecolab)
[2]DOWANOL DPM ™ (Dow Chemical Co.)
[3]DOWANOL PPH ™ (Dow Chemical Co.)
[4]DOWANOL DPNP ™ (Dow Chemical Co.)
[5]DBE-3 ™ (Dupont Nylon)
[6]DOWANOL EPH ™ (Dow Chemical Co.)
[7]Neutralized to pH = 3.7 with acetic acid.

The compositions in Run Nos. 3-3 to 3-18 exhibited phase-splitting. The results in Table III demonstrate that substantial improvements in antimicrobial efficacy could be obtained by modifying all three commercial aseptic wash products, as can be seen by comparing control Run No. 3-1 with Run Nos. 3-4 through 3-7, 3-9 through 3-13 and 3control Run No. 3-2 with Run Nos. 3-16 and 3-17; and control Run No. 3-3 with Run No. 3-18. Run Nos. 3-8 and 3-14 exhibited significant antimicrobial efficacy without an antimicrobial agent.

A composition containing both a sparingly soluble antimicrobial solvent and an antimicrobial agent exhibited a synergistic improvement in performance compared to the use of either the antimicrobial solvent or the antimicrobial agent alone, as can be seen by comparing Run No. 3-10with Run Nos. 3-1 and 3-8.

Example 4

Using the method of Example 2, varying amounts of several sparingly soluble solvents were added to commercial peracid bottle washing formulations (TSUNAMI-100™, MATRIXX™, or KX-6091; Ecolab) and tested against the mold *C. funicola* using a 10 second contact time at 60° C. The surfactant dodecylbenzene sulfonate ("DBS") was added to some of the compositions to slow down, but not inhibit, phase-splitting.

Set out below in Table IV are the run number, solvent, solvent concentration, peracid concentration, DBS concentration, appearance of the mixtures after they had been allowed to stand for 1 minute, and observed log order reduction for *C. funicola* for each composition.

TABLE IV

| Run No. | Solvent | Solvent (%) | Peracid (ppm) | DBS[7] (ppm) | Appearance | *C. funicola* Log Reduction |
|---|---|---|---|---|---|---|
| 4-1 | Benzyl alcohol | 10% | 2000[1] | 1000 | cloudy (2-phase) | >4.4 |
| 4-2 | Benzyl alcohol | 10% | 2000[1] | 0 | cloudy (2-phase) | 3.9 |
| 4-3 | Benzyl alcohol | 5% | 2000[1] | 500 | cloudy (2-phase) | 4.1 |
| 4-4 | Benzyl alcohol | 1% | 2000[1] | 100 | clear (1-phase) | 0.1 |
| 4-5 | None | 0% | 2000[1] | 0 | clear (1-phase) | 0.1 |
| 4-6 | DBE ™ Diester blend[2] | 10% | 2000[1] | 1000 | cloudy (2-phase) | >4.4 |
| 4-7 | DBE ™ Diester blend[2] | 10% | 2000[1] | 0 | cloudy (2-phase) | >4.4 |
| 4-8 | DBE ™ Diester blend[2] | 5% | 2000[1] | 500 | cloudy (2-phase) | 4.2 |
| 4-9 | DBE ™ Diester blend[2] | 2.5% | 1500[6] | 0 | hazy (2-phase) | >4.4 |
| 4-10 | DBE ™ Diester blend[2] | 2.5% | 1200[6] | 0 | hazy (2-phase) | >4.4 |
| 4-11 | DBE ™ Diester blend[2] | 1% | 2000[3] | 100 | hazy (2-phase) | 1.2 |
| 4-12 | None | 0% | 2000[6] | 0 | clear (1 phase) | 0.2 |
| 4-13 | DBE-3 ™ Diester blend[2] | 5% | 1000[4] | 1000 | cloudy (2-phase) | >4.4 |
| 4-14 | DBE-3 ™ Diester blend[2] | 4% | 1000[4] | 0 | cloudy (2-phase) | >4.4 |
| 4-15 | DBE-3 ™ Diester blend[2] | 3% | 1000[3] | 0 | cloudy (2-phase) | 3.2 |
| 4-16 | DBE-3 ™ Diester blend[2] | 2% | 1000[3] | 0 | hazy (2-phase) | 3.1 |
| 4-17 | DBE-3 ™ Diester blend[2] | 2.5% | 1500[6] | 0 | hazy (2-phase) | >4.4 |
| 4-18 | None | 0% | 1000[3] | 0 | clear (1-phase) | 0.05 |
| 4-19 | Solvent Mixture[5] | 5% | 2000[1] | 0 | cloudy (2-phase) | 3.6 |
| 4-20 | Solvent Mixture[5] | 1% | 2000[1] | 0 | clear (1 phase) | 0.6 |
| 4-21 | Phenoxyethanol | 5.0% | 2000[3] | 0 | cloudy (2-phase) | 4.8 |
| 4-22 | Phenoxyethanol | 5.0% | 2000[6] | 0 | cloudy (2-phase) | 3.9 |
| 4-23 | Phenoxyethanol | 2.5% | 1200[6] | 0 | hazy (2-phase) | 3.0 |
| 4-24 | Phenoxyethanol | 2.5% | 1500[6] | 0 | hazy (2-phase) | >4.0 |
| 4-25 | Phenylethanol | 3.0% | 2000[6] | 0 | cloudy (2-phase) | >4.5 |
| 4-26 | Tetrabutyl ammonium hydroxide, pH = 3.7 | 5.0% | 2000[6] | 0 | cloudy (2-phase) | >4.5 |

TABLE IV-continued

| Run No. | Solvent | Solvent (%) | Peracid (ppm) | DBS[7] (ppm) | Appearance | *C. funicola* Log Reduction |
|---|---|---|---|---|---|---|

[1]TSUNAMI-100 ™ commercial peracid (Ecolab)
[2]Diester Blends (Dupont Nylon)
[3]MATRIXX ™, mixed peracids (Ecolab)
[4]KX-6091 commercial peracid (Ecolab)
[5]Mixture containing 50% benzyl alcohol, 15% DOWANOL PPH ™ glycol solvent (Dow Chemical Co.), 15% BUTYL CARBITOL ™, 15% DOWANOL DPNB ™ glycol solvent (Dow Chemical Co.) and 5% SURFONIC 24-9 ™ nonionic surfactant (Huntsman Chemicals)
[6]15C commercial peracid (Ecolab)
[7]Dodecyl benzene sulfonic acid For each of the antimicrobial compositions in Table IV, significant antimicrobial efficacy was obtained near, or just above, the solubility limit of the antimicrobial solvent in the diluting solvent. The results in Table IV show that substantial improvements in antimicrobial efficacy were obtained by modifying the commercial aseptic wash products, as can be seen by comparing control Run No. 4-5 with Run Nos. 4-1 through 4-3 and 4-19; control Run No. 4-12 with Run Nos. 4-6 through 4-11 and 4-22; and control Run No. 4-18 with Run Nos. 4-13 through 4-17. Compositions with and without added surfactant (DBS) exhibited increased antimicrobial activity, as can be seen, for example, from Run Nos. 4-1 through 4-3 and 4-6 through 4-11. Compositions containing mixtures of antimicrobial solvents are shown in Run Nos. 4-19 and 4-20.

Example 5

Using the method of Example 2, varying amounts of benzyl alcohol were added to commercial peracid bottle washing formulations (KX-6091, 15C, TSUNAMI-100™, and VORTEXX™; Ecolab) and tested against the spore-forming, enterotoxin producing pathogen *Bacillus cereus* and the mold *C. funicola* using a 10 second contact time at 60° C.

Set out below in Table V are the run number, solvent, solvent concentration, peracid concentration, appearance of the mixtures after they had been allowed to stand for 1 minute, and the observed log order reduction for *Bacillus cereus* and *C. funicola* for each composition.

TABLE V

| | | | | | Log Reduction | |
|---|---|---|---|---|---|---|
| Run No. | Solvent | Solvent (%) | Peracid[1] (ppm) | Appearance | *B. Cereus* | *C. funicola* |
| 5-1 | None | 0% | 1000[1] | clear | 1.2 | 0.1 |
| 5-2 | None | 0% | 2000[1] | clear | 6.2 | 0.2 |
| 5-3 | None | 0% | 2000[2] | clear | — | 0.1 |
| 5-4 | None | 0% | 2000[3] | clear | 0.2 | 0.2 |
| 5-5 | None | 0% | 2000[4] | clear | 0.1 | 0.1 |
| 5-6 | Benzyl alcohol | 10% | 0 | very cloudy[5] | — | >4.4 |
| 5-7 | Benzyl alcohol | 10% | 1000[1] | very cloudy[5] | — | >4.4 |
| 5-8 | Benzyl alcohol | 4.5% | 0 | very cloudy[5] | 0.1 | >4.4 |
| 5-9 | Benzyl alcohol | 4.5% | 1000[1] | very cloudy[5] | 6.3 | >4.4 |
| 5-10 | Benzyl alcohol | 4.0% | 0 | very cloudy[6] | — | >4.4 |
| 5-11 | Benzyl alcohol | 4.0% | 1000[1] | very cloudy[6] | 3.6 | >4.4 |
| 5-12 | Benzyl alcohol | 4.0% | 1000[3] | very cloudy[6] | 4.8 | >4.4 |

TABLE V-continued

| | | | | | Log Reduction | |
|---|---|---|---|---|---|---|
| Run No. | Solvent | Solvent (%) | Peracid[1] (ppm) | Appearance | *B. Cereus* | *C. funicola* |
| 5-13 | Benzyl alcohol | 3.5% | 0 | opaque[6] | — | 4.2 |
| 5-14 | Benzyl alcohol | 3.5% | 1000[1] | opaque[6] | 1.8 | >4.4 |
| 5-15 | Benzyl alcohol | 3.5% | 1000[2] + 1500[2] | clear | >6.3 | >4.4> |
| 5-16 | Benzyl alcohol | 3.5% | 2000[2] | clear | >6.3 | 4.5 |
| 5-17 | Benzyl alcohol | 3.5% | 1500[3] | clear | >6.3 | >4.5 |
| 5-18 | Benzyl alcohol | 3.5% | 0 | cloudy[5] | 3.4 | 2.6 |
| 5-19 | Benzyl alcohol | 3.0% | 1000[1] | clear | — | 2.7 |
| 5-20 | Benzyl alcohol | 3.0% | 1000[2] | clear | >6.5 | 3.8 |
| 5-21 | Benzyl alcohol | 3.0% | 2000[2] | clear | >6.3 | >4.7 |
| 5-22 | Benzyl alcohol | 3.0% | 2500[2] | clear | >6.3 | >4.5 |
| 5-23 | Benzyl alcohol | 3.0% | 1500[2] | clear | >6.3 | >4.5 |
| 5-24 | Benzyl alcohol | 3.0% | 1000[3] | clear | >6.5 | 4.3 |
| 5-25 | Benzyl alcohol | 3.0% | 1000[4] | cloudy[5] | >6.5 | 4.0 |
| 5-26 | Benzyl alcohol | 3.0% | 1000[1] | hazy | >6.2 | 4.0 |
| 5-27 | Benzyl alcohol | 2.5% | 1000[3] | clear | 6.4 | 4.2 |
| 5-28 | Benzyl alcohol | 2.5% | 1000[1] | cloudy[5] | 3.0 | 4.0 |
| 5-29 | Benzyl alcohol | 2.0% | 1000[3] | clear | 4.3 | 2.3 |
| 5-30 | Benzyl alcohol | 2.0% | 1000[2] | cloudy[5] | 4.7 | 4.0 |
| 5-31 | Benzyl alcohol | 2.0% | 1000[1] | clear | 3.7 | 3.8 |
| 5-32 | Benzyl alcohol | 1.5% | 1000[3] | clear | 5.9 | 1.2 |
| 5-33 | Benzyl alcohol | 1.5% | 0 | cloudy[5] | 0.05 | 0.2 |

[1]KX-6091 commercial peracid (Ecolab)
[2]15C commercial peracid (Ecolab)
[3]VORTEXX ™ commercial peracid (Ecolab)
[4]TSUNAMI-100 ™ commercial peracid (Ecolab)
[5]Rapid phase separation.
[6]Slow phase separation.

The results in Table V show substantial enhancement in antimicrobial efficacy for compositions both above and below the water solubility limit (as evidenced visually by solution clarity) of the antimicrobial solvent in the diluting solvent. Significant antimicrobial efficacy was also obtained against. both organisms using some clear solutions (see, e.g., Run Nos. 5-15 through 5-17, 5-20 through 5-24, 5-27, 5-29, 5-31 and 5-32).

Example 6

Aqueous mixtures containing 3% or 1% benzyl alcohol solvent and 2000 ppm or 1000 ppm of a commercial peracid bottle washing formulation (KX-6091 or VORTEXX™; Ecolab) were prepared. A surfactant was added to some of the mixtures. The mixtures were tested against the mold *C. funicola* using a 10 second contact time at 60° C.

Set out below in Table VI are the run number, solvent concentration, peracid, surfactant, appearance of the mixtures after they had been allowed to stand for 1 minute, and the observed log order reduction for *C. funicola* for each composition.

TABLE VI

| Run No. | Benzyl Alcohol, % | Peracid (ppm) | Surfactant | Appearance | C. funicola Log Reduction |
|---|---|---|---|---|---|
| 6-1 | (3%) | 2000 ppm[1] | None | cloudy, phase separating | 3.4 |
| 6-2 | (3%) | 2000 ppm[1] | mixed[2] | clear, 1-phase microemulsion | 0.2 |
| 6-3 | (1%) | 1000 ppm[3] | None | clear, 1-phase | 0.2 |
| 6-4 | (1%) | 1000 ppm[3] | LAS-MIPA[4] | cloudy, phase separating | 2.8 |

[1]KX-6091 commercial peracid (Ecolab)
[2]1000 ppm of a mixture of 20% mineral oil, 40% alkyl polyglucoside, and 40% alcohol ethoxylate containing five ethylene oxide units.
[3]VORTEXX ™ commercial peracid (Ecolab)
[4]1000 ppm monoisopropanol amine salt of linear alkylbenzene sulfonate.

The mixed surfactant reduced antimicrobial efficacy, as can be seen by comparing Run Nos. 6-1 and 6-2. The sulfonate surfactant improved antimicrobial efficacy, as can be seen by comparing Run Nos. 6-3 and 6-4.

Example 7

Using the method of Example 2, varying amounts of sparingly soluble solvent blends were added to a peracid bottle washing formulation (15C; Ecolab) and tested against spores of *Bacillus subtilis* and the mold *C. funicola* using a 10 second contact time at 60° C.

Set out below in Table VII are the run number, solvents, solvent concentrations, peracid concentration, appearance of the mixtures after they had been allowed to stand for 1 minute, and the observed log order reduction for *Bacillus cereus* and *C. funicola* for each composition.

TABLE VII

| Run No. | Solvent(s) | Solvent (%) | Peracid[1] (ppm) | Appear-ance | Log Reduction B. subtilis | C. funicola |
|---|---|---|---|---|---|---|
| 7-1 | Diester blend[2] | 2.5 | 1500 | hazy | >6.5 | >4.4 |
| 7-2 | Benzyl alcohol | 3.5 | 1000 | hazy | 6.1 | 5.2 |
| 7-3 | Diester blend[2] | 1.5 | 0 | clear | 0 | >4.4 |
| | benzyl alcohol | 1.0 | | | | |
| 7-4 | Diester blend[2] | 1.0 | 0 | clear | 0 | >4.4 |
| | benzyl alcohol | 1.5 | | | | |
| 7-5 | Diester blend[2] | 1.0 | 1500 | clear | >6.0 | >4.4 |
| | benzyl alcohol | 1.5 | | | | |
| 7-6 | Diester blend[2] | 1.5 | 1500 | clear | >6.0 | >4.4 |
| | benzyl alcohol | 1.0 | | | | |

[1]15C commercial peracid (Ecolab)
[2]DBE-3 ™ (DuPont Nylon)

The results in Table VII show substantial enhancement in antimicrobial efficacy for compositions both above and below the water solubility limit (as evidenced visually by solution clarity) of the antimicrobial solvent. Most notable are the blended solvent systems shown in Run Nos. 7-5 and 7-6, which utilized each solvent below its solubility limit and a peracid, and provided significant broad-spectrum antimicrobial efficacy using clear solutions.

Example 8

Using the method of Example 2, a sparingly soluble solvent was added to various antimicrobial agents and tested against *Bacillus cereus, Bacillus subtilis, C. funicola* and *N. fisheri* using a 10 second contact time at 60° C.

Set out below in Table VIII are the run number, solvent and antimicrobial agent employed, solvent amount, antimicrobial agent amount, and the observed log order reduction for *Bacillus cereus, Bacillus cereus, C. funicola*, or *N. fisheri* for each composition.

TABLE VIII

| Run No. | Solvent + Antimicrobial Agent(s) | Solvent Amount | Antimicrobial Agent Amount | Log Reduction B. cereus | B. subtilis | C. funicola | N. fisheri |
|---|---|---|---|---|---|---|---|
| 8-1 | Diester blend[1] + NaOCl[5] | 2.5% | 200 ppm | >6.3 | >6.0 | >4.4 | >4.6 |
| 8-2 | Diester blend[1] + NaOCl[5] | 2.5% | 400 ppm | — | >6.0 | >4.4 | — |
| 8-3[2] | Diester blend[1] + $H_2O_2$ | 5.0% | 2.1% | — | 2.9 | >4.4 | 2.1 |
| 8-4[2] | Diester blend[1] + $H_2O_2$ | 5.0% | .2% | — | >6.0 | >4.4 | — |
| 8-5 | Diester blend[1] + $C_8$FA[3] + POAA[4] | 2.5% | 800 + 1500 ppm | — | — | >4.8 | — |
| 8-6 | Diester blend[1] | 1.5% | 0 | — | — | 0.2 | — |
| 8-7 | $C_8$FA[3] | 800 ppm | 0 | — | — | 0.2 | — |
| 8-8 | POAA[4] | 1500 ppm | 0 | — | — | 0.2 | — |

[1]DBE-3 ™ (Dupont Nylon)
[2]The solution was aged >18 hours prior to use.
[3]$C_8$FA = octanoic acid.
[4]POAA = peroxyacetic acid.
[5]Acidified to pH = 6.0 with acetic acid.

The results in Table VIII illustrate use of various two solvent antimicrobial compositions including diluting solvent, a solvent only partially or sparingly soluble in that solvent and also including antimicrobial agent. The mixture shown in Run No. 8-5 gave an especially synergistic result compared to the three control compositions of Run Nos. 8-6 through 8-8.

Example 9

Using the method of Example 2, a composition was tested against the spore *Bacillus cereus* and the mold *C. funicola* using a 120 second contact time at 40° C. These experiments were run to determine the antimicrobial effectiveness at a lower treatment temperature of a two solvent antimicrobial composition including diluting solvent and a solvent only partially or sparingly soluble in that solvent.

Set out below in Table IX are the run number, solvent and antimicrobial agent, solvent amount, antimicrobial agent amount, and the observed log order reduction for *Bacillus cereus* and *C. funicola* for each composition.

TABLE IX

| Run No. | Solvent + Antimicrobial Agent | Solvent (%) | Antimicrobial Agent Amount | Log Reduction *B. cereus* | Log Reduction *C. funicola* |
|---|---|---|---|---|---|
| 9-1 | Diester blend[1] + NaOCI | 2.5% | 200 ppm | >6.3 | 3.2 |
| 9-2[2] | Diester blend[1] + $H_2O_2$ | 3.0% | 0.84% | >6.3 | 1.0 |
| 9-3[2] | Diester blend[1] + $H_2O_2$ | 2.5% | .70% | >6.3 | 1.0 |
| 9-4 | Diester blend[1] + POAA[3] | 2.5% | 1500 ppm | >6.3 | 2.7 |

[1]DBE-3 ™ (Dupont Nylon)
[2]The solution was aged >18 hours prior to use.
[3]Peroxyacetic acid The results in Table IX demonstrate the ability of two solvent antimicrobial compositions including diluting solvent and a solvent only partially or sparingly soluble in that solvent to effectively reduce microbial growth at lower treatment temperatures.

Example 10

Aqueous mixtures containing a sparingly soluble antimicrobial solvent, a peracid, or mixtures of both were prepared and evaluated against the spore-forming, enterotoxin producing pathogen *Bacillus cereus* using a 10 second contact time at 60° C.

Set out below in Table X are the run number, solvent, solvent concentration, peracid concentration, and the observed log order reduction for *B. cereus* for each composition.

TABLE X

| Run No. | Solvent | Solvent, (wt %) | Peracid (ppm) | *B. cereus* Log Reduction |
|---|---|---|---|---|
| 10-1 | None | 0% | 1000[1] | 0.2 |
| 10-2 | None | 0% | 3000[1] | 0.9 |
| 10-3 | None | 0% | 4000[2] | 0.8 |
| 10-4 | Benzyl alcohol | 3% | 0 | 0.1 |
| 10-5 | Benzyl alcohol | 3% | 1000[1] | 2.4 |
| 10-6 | Diester blend[4] | 3% | 0 | 0.3 |
| 10-7 | Diester blend[4] | 3% | 1000[2] | 3.6 |
| 10-8 | Diester blend[4] | 2.5% | 1500[3] | >6.3 |

[1]OXONIA ACTIVE ™ commercial peracid (Ecolab)
[2]MATRIXX ™ commercial peracid (Ecolab)
[3]15C commercial peracid (Ecolab)
[4]DBE-31 ™ (Dupont Nylon)

The results in Table X show the substantial improvements in sporicidal efficacy that can be obtained by combining the antimicrobial solvent and a peracid, as can be seen by comparing Run Nos. 10-1, 10-4 and 10-5, and Run Nos. 10-3, 10-6 and 10-7. This improvement is greater than additive and possibly synergistic. Run No. 10–7 provided nearly a 3-log reduction improvement compared to the use of the antimicrobial solvent or peracid alone, while using a lower quantity of peracid. Run No. 10-8 provided an especially effective sporicide at even lower levels of antimicrobial solvent and peracid.

Example 11

Using the method of Example 10, aqueous mixtures containing 3% benzyl alcohol, or varying amounts of several peracids (KX-6091, MATRIXX™, TSUNAMI 100™ or OXONIA ACTIVE™; Ecolab), or mixtures of both benzyl alcohol and peracid were prepared and evaluated as possible sterilant formulations against the spore-forming, enterotoxin producing pathogen *Bacillus cereus* using a 10 second contact time at 60° C.

Set out below in Table VIII are the run number, solvent, peracid concentration, and the observed log order reduction for *B. cereus* for each composition.

TABLE XI

| Run No. | Solvent | Solvent, (wt %) | Peracid, (ppm) | *B. cereus* Log Reduction |
|---|---|---|---|---|
| 11-1 | Benzyl alcohol | 3% | 1000[1] | >6.5 |
| 11-2 | Benzyl alcohol | 3% | 1000[2] | >6.5 |
| 11-3 | Benzyl alcohol | 3% | 1000[3] | >5.6 |
| 11-4 | Benzyl alcohol | 3% | 1000[4] | 2.4 |
| 11-5 | Benzyl alcohol | 3% | 1000[5] | >6.3 |
| 11-5 | Benzyl alcohol | 3% | None | 0.1 |
| 11-6 | None | 0% | 4000[4] | 0.8 |
| 11-7 | None | 0% | 4000[2] | 0.8 |

[1]KX-6091 commercial peracid (Ecolab)
[2]MATRIXX ™, mixed peracid (Ecolab)
[3]TSUNAMI-100 ™ commercial peracid (Ecolab)
[4]OXONIA ACTIVE ™ commercial peracid (Ecolab)
[5]15C commercial peracid (Ecolab)

The results in Table XI show the substantial synergistic improvements in sporicidal efficacy that can be obtained by combining the antimicrobial solvent and a peracid. For example, Run No. 11-2 provided more than a 6-log reduction improvement compared to the use of the antimicrobial solvent alone (Run No. 11-5), and nearly a 6-log reduction improvement compared to the use of the peracid alone (Run No. 11-7), yet required only one-fourth as much peracid.

Example 12

Using the method of Example 10, aqueous mixtures containing various sparingly soluble solvents and varying amounts of a peracid (15C; Ecolab) were prepared and evaluated against the spore-forming, enterotoxin producing pathogen *Bacillus cereus* using a 10 second contact time at 60° C.

Set out below in Table XII are the run number, solvent type and concentration, peracid type and concentration, and the observed log order reduction for *B. cereus* for each composition. As shown, a wide range of chemical solvent classes yielded substantial spore reductions.

TABLE XII

| Run No. | Solvent Type and Amount (wt %) | Peracid Type and Amount (ppm) | *B. cereus* Log Reduction |
|---|---|---|---|
| 12-1 | Phenoxyethanol (2.5%) | 15C[1] (1200 ppm) | 3.4 |
| 12-2 | Phenethanol (3.0%) | 15C[1] (2000 ppm) | >6.4 |
| 12-3 | Benzoic acid (0.5%) | 15C[1] (2000 ppm) | >6.0 |
| 12-4 | Benzyl benzoate (0.5%) | 15C[1] (2000 ppm) | 2.3 |
| 12-5 | Diester blend[2] (2.5%) | 15C[1] (1200 ppm) | >6.2 |

TABLE XII-continued

| Run No. | Solvent Type and Amount (wt %) | Peracid Type and Amount (ppm) | *B. cereus* Log Reduction |
|---|---|---|---|

[1]15C commercial peracid (Ecolab)
[2]DBE-3 ™ (Dupont Nylon)

Example 13

Using the method of Example 10, aqueous mixtures containing varying types and amounts of sparingly soluble solvents and varying types and amounts of several peracids were prepared and evaluated as sporicides against *Bacillus subtilis*, using a 10 second contact time at 60° C.

Set out below in Table XIII are the run number, solvent, solvent concentration, peracid type and concentration, and the observed log order reduction for *B. subtilis* for each composition.

TABLE XIII

| Run No. | Solvent | Solvent wt % | Peracid Type and Amount, ppm | *B. subtilis* Log Reduction |
|---|---|---|---|---|
| 13-1 | Benzyl alcohol | 3.0% | VORTEXX ™[1] (1000 ppm) | >6.7 |
| 13-2 | Benzyl alcohol | 3.0% | VORTEXX ™[1] (1500 ppm) | >6.7 |
| 13-3 | Benzyl alcohol | 3.5% | VORTEXX ™[1] (1000 ppm) | >6.7 |
| 13-4 | Benzyl alcohol | 3.0% | VORTEXX ™[1] (1500 ppm) | >6.7 |
| 13-5 | Benzyl alcohol | 3.5% | 15C[2] (1000 ppm) | 5.6 |
| 13-6 | Benzyl alcohol | 2.5% | VORTEXX ™[1] (1500 ppm) | >6.7 |
| 13-7 | Benzyl alcohol | 2.0% | VORTEXX ™[1] (1500 ppm) | >6.7 |
| 13-8[4] | Benzyl alcohol | 2.0% | TSUNAMI 100 ™[3] (1000 ppm) | >6.7 |
| 13-9 | Phenoxyethanol | 5.0% | 15C[2] (1000 ppm) | 6.7 |
| 13-10 | Phenoxyethanol | 5.0% | VORTEXX ™[1] (1000 ppm) | 6.7 |
| 13-11 | Phenoxyethanol | 2.5% | 15C[2] (1500 ppm) | >6.5 |
| 13-12 | Phenoxyethanol-tetra ethoxylate | 5.0% | 15C[2] (1000 ppm) | 6.7 |
| 13-13 | Diester blend[5] | 2.5% | 15C[2] (1500 ppm) | >6.5 |
| 13-14 | Diester blend[5] | 1.5% | VORTEXX ™[1] (1500 ppm) | >6.7 |
| 13-15 | Tert-butanol | 5.0% | VORTEXX ™[1] (1500 ppm) | >6.7 |

[1]VORTEXX ™, mixed peracid (Ecolab)
[2]15C commercial peracid (Ecolab)
[3]TSUNAMI 100 ™ commercial peracid (Ecolab)
[4]Also contained 1000 ppm sodium octyl sulfonate
[5]DBE-3 ™ (Dupont Nylon)

Example 14

Using the method of Example 2, aqueous mixtures containing 2.5 wt.% DBE-3™ solvent (diester blend, DuPont Nylon) and a peracid were prepared and evaluated as a general antimicrobial agent against *S. aureus, E. coli*, or *N. fisheri* using a 10 second contact time at 60° C.

Set out below in Table XIV are the run number, peracid type and amount, and the observed log order reduction for each organism.

TABLE XIII

| Run No. | Peracid Type and Amount (ppm) | Log Reduction *S. aureus* | *E. coli* | *N. fisheri* |
|---|---|---|---|---|
| 14-1 | 15C[1] (2000 ppm) | — | — | 3.7 |
| 14-2 | OXONIA ACTIVE ™[2] (75 ppm) | >7.2 | >7.1 | — |

[1]Commercial peracid (Ecolab)
[2]Commercial peracid (Ecolab)

Example 15

Aqueous non-phase separating mixtures containing various levels of an antimicrobial solvent (dibasic esters) along with various levels of commercial peracid bottle rinsing formulations were prepared. A surfactant was added to some of the mixtures. The mixtures were tested against the mold *C. funicola* using a 10 second contact time at 60° C.

Set out below in Table XIV are the run number, solvent, solvent concentration, peracid concentration, surfactant, appearance of the mixtures after they had been allowed to stand for at least 1 minute, and the observed log order reduction for *C. funicola* for each composition.

TABLE XIV

| Formulation Number | Solvent | Solvent % | Peracid (ppm) | Added Surfactant | Appearance | *C. funicola* Log Reduction |
|---|---|---|---|---|---|---|
| | | | Control Formulations | | | |
| 1-1 | none | 0% | 1000 ppm[2] | none | clear, 1-phase | 0.05 |
| 1-2 | none | 0% | 2000 ppm[4] | none | clear, 1-phase | 0.2 |
| 1-3 | BzOH | 1% | 1000 ppm[2] | none | clear, 1-phase | 0.2 |
| 1-4 | BzOH | 3% | 2000 ppm[1] | none | cloudy, phase separating | 3.4 |
| 1-5 | BzOH | 3% | 2000 ppm[1] | mixed[7] | clear, 1-phase | 0.2 |

TABLE XIV-continued

| Formulation Number | Solvent | Solvent % | Peracid (ppm) | Added Surfactant | Appearance | C. funicola Log Reduction |
|---|---|---|---|---|---|---|
| 1-6 | DBE ™[6] | 2.5% | 1500 ppm[3] | none | microemulsion | >4.4 |
| 1-7 | DBE ™[6] | 2.5% | 1200 ppm[3] | none | hazy (2-phase) | >4.4 |
| 1-8 | DBE ™[6] | 1% | 2000 ppm[3] | 100 ppm[8] | hazy (2-phase) | 1.2 |
| 1-9 | DBE-3 ™[6] | 2% | 1000 ppm[2] | none | hazy (2-phase) | 3.1 |
| 1-10 | DBE-3 ™[6] | 2.5% | 1500 ppm[3] | none | hazy (2-phase) | >4.4 |
| 1-11 | DBE-3 ™[6] | 1.5% | 1500 ppm[2] | none | hazy (2-phase) | >3.8 |
| | | | | | hazy (2-phase) | |
| | | | Inventive Formulations | | | |
| 1-12 | DBE-3 ™[6] | 1% | 1000 ppm[5] | none | clear, 1-phase | 0.9 |
| 1-13 | DBE-3 ™[6] | 1% | 2000 ppm[5] | none | clear, 1-phase | 3.2 |
| 1-14 | DBE-3 ™[6] | 2.5% | 1000 ppm[5] | none | clear, 1-phase | >4.5 |
| 1-15 | DBE-3 ™[6] | 2.5% | 2000 ppm[5] | none | clear, 1-phase | >4.5 |
| 1-16 | DBE-6 ™[6] | 1% | 1000 ppm[5] | none | clear, 1-phase | 1.0 |
| 1-17 | DBE-6 ™[6] | 1% | 2000 ppm[5] | none | clear, 1-phase | 3.3 |
| 1-18 | DBE-6 ™[6] | 2.5% | 1000 ppm[5] | none | clear, 1-phase | >4.5 |
| 1-19 | DBE-6 ™[6] | 2.5% | 2000 ppm[5] | none | clear, 1-phase | >4.5 |

[1]KX-6091 experimental peracid (Ecolab)
[2]VORTEXX ™ commercial peracid (Ecolab)
[3]15C experimental peracid (Ecolab)
[4]Tsunami-100 ™ commercial peracid (Ecolab)
[5]KX-6138 experimental peracid (Ecolab)
[6]Diester blends (Dupont Nylon)
[7]1000 ppm of a mixture of 20% mineral oil, 40% alkyl polyglucoside, and 40% alcohol ethoxylate containing five ethylene oxide units.
[8]Active ppm's of dodecylbenzene sulfonic acid, 97%.

The results in Table XIV show improved efficacy results for the present non-phase separating compositions as compared to the controls which either separate or are coupled but without biocidal activity.

Example 16

As in the previous example several non-phase separating compositions were made using various antimicrobial solvents at 1 or 2.5 wt %, along with 1000 or 2000 ppm of a peracid bottle washing formulation (KX-6138, Ecolab). The mixtures were tested against the mold *C. funicola* and spores of *B. cereus* using a 10 second contact time at 60° C.

Set out below in Table XV are the run number, solvent, solvent concentration, peracid concentration, appearance of the mixtures after they had been allowed to stand for 5 minutes, and the observed log order reduction for *C. funicola* and *B. cereus* for each composition.

TABLE XV

| Formulation Number | Solvent | Solvent % | Peracid (ppm) | Appearance | C. funicola Log Reduction | B. cereus Log Reduction |
|---|---|---|---|---|---|---|
| 1-12 | DBE-3 ™[1] | 1% | 1000 ppm | clear, 1-phase | 0.9 | 1.0 |
| 1-13 | DBE-3 ™[1] | 1% | 2000 ppm | clear, 1-phase | 3.2 | 2.3 |
| 1-14 | DBE-3 ™[1] | 2.5% | 1000 ppm | clear, 1-phase | >4.5 | 2.9 |
| 1-15 | DBE-3 ™[1] | 2.5% | 2000 ppm | clear, 1-phase | >4.5 | 5.8 |
| 1-16 | DBE-6 ™[1] | 1% | 1000 ppm | clear, 1-phase | 1.0 | 1.1 |
| 1-17 | DBE-6 ™[1] | 1% | 2000 ppm | clear, 1-phase | 3.3 | 2.3 |
| 1-18 | DBE-6 ™[1] | 2.5% | 1000 ppm | clear, 1-phase | >4.5 | 1.5 |
| 1-19 | DBE-6 ™[1] | 2.5% | 2000 ppm | clear, 1-phase | >4.5 | 6.5 |

[1]DBE-6 ™ from Dupont Nylon.

Table XV shows the effectiveness of the non-phase separating compositions against multiple aseptic test organisms.

Example 17

To determine effective ratios of adipate/succinate/glutarate ester concentrations in the two solvent compositions, various mixtures were prepared and tested as in the earlier examples. Diester dicarboxylate mixtures containing dimethyl adipate, dimethyl succinate, and dimethyl glutarate at a total concentration of 2.5 wt % were added to a 2000 ppm peracid bottle washing formulation (KX-6138, Ecolab). These two solvent compositions were tested against spores of *Bacillus cereus* and the mold *C. funicola* using a 10 second contact time at 60° C.

Set out below in Table XVI are the run number, dimethyl adipate wt %, dimethyl succinate wt %, dimethyl glutarate wt %, the appearance of the mixtures after they had been allowed to stand for 5 minutes, and the observed log order reduction for *C. funicola* and spores of *Bacillus cereus* for each composition.

TABLE XVI

| Formulation Number | dimethyl adipate wt% | dimethyl succinate wt% | dimethyl glutarate wt% | Appearance | *C. funicola* Log Reduction | *B. cereus* Log Reduction |
|---|---|---|---|---|---|---|
| 3-1 | 0.0% | 2.5% | 0.0% | clear, 1-phase | 1.8 | 1.6 |
| 3-2 | 0.0% | 0.0% | 2.5% | clear, 1-phase | 4.5 | 2.6 |
| 3-3 | 2.2% | 0.0% | 0.3% | clear, 1-phase | 4.5 | 5.8 |
| 3-4 | 2.5% | 0.0% | 0.0% | clear, 1-phase | 4.5 | 6.5 |

Table XVI shows the overwhelming biocidal effectiveness of using the dimethyl adipate derivative in the non-phase separating compositions. As the concentration adipate increases in the mixture there is an increase antimicrobial improvement against a multiple of aseptic test organisms.

Example 18

Using the method of the previous examples, various wt %'s of antimicrobial diester dicarboxylate solvent (DBE-3™), which contains dimethyl adipate, was added to a 1500 ppm solution of ester peroxycarboxylic acid being commercialized under the trade name Perestane (SOLVAY S.A.). This composition was tested against spores of *Bacillus* spp. and the mold *C. funicola* using a 10 second contact time at 60° C.

Set out below in Table XVII are the formulation number, solvent wt-%, peracid concentrations, surfactants added, appearance of the mixtures after they had been allowed to stand for 1 minute, and the observed log order reduction for and *C. funicola* and spores of *Bacillus* spp. for each composition.

TABLE XVII

| Formulation Number | Solvent % | Peracid (ppm) | Added Surfactant | Appearance | *C. funicola* Log Reduction | *Bacillus* spp.[1] Log Reduction |
|---|---|---|---|---|---|---|
| | | | Control Formulations | | | |
| 4-1 | 0% | 4000 ppm | None | clear, 1-phase | 0.2 | 0.6 |
| 4-2 | 0% | 2000 ppm | L61[3] | clear, 1-phase | 0.2 | 0.2 |
| 4-3 | 0% | 4000 ppm | L61[3] | clear, 1-phase | 0.3 | 0.7 |
| 4-4 | 0% | 2000 ppm | mixed[4] | clear, 1-phase | 0.2 | 0.2 |
| 4-5 | 0% | 4000 ppm | mixed[4] | clear, 1-phase | 0.2 | 0.4 |
| 4-6 | 0% | 2000 ppm | mixed[4] | clear, 1-phase | 0.2 | 0.4 |
| 4-7 | 0% | 4000 ppm | mixed[4] | clear, 1-phase | 0.2 | 1.2 |
| | | | Inventive Formulations | | | |
| 4-8 | 1% | 1500 ppm[4] | none | clear, 1-phase | 0.2 | >4.2 |
| 4-9 | 2.5% | 1500 ppm[4] | none | clear, 1-phase | 1.1 | >4.2 |

[1]Either *Bacillus cereus* or *Bacillus subtilis*.
[2]As described in PCT patent application publication WO 9828267(A1).
[3]1429 ppm of Pluronic L61 from BASF.
[4]1429 ppm of Pluronic L61 from BASF and 476 ppm of dodecylbenzene sulfonic acid.
[5]1190 ppm of Pluronic L61 from BASF and 1190 ppm of dodecylbenzene sulfonic acid.

Table XVII demonstrates the effectiveness of non-phase separating biocidal compositions containing mono-ester dicarboxylate peracids.

Example 19

Using methods employed in the previous examples, two solvent antimicrobial compositions including various diester dicarboxylate antimicrobial solvents were tested against *C. funicola* and *B. cereus*. These two solvent compositions included diester dicarboxylates of various chain lengths, both in the portion of the ester derived from the carboxylic acid and the portion derived from the alcohol. In each case, the peroxycarboxylic acid employed was Ecolab's KX 6138.

The following table lists the components of the compositions and the log kill against the two microorganisms.

TABLE XVIII

| Solvent type | Phases | Solvent wt-% | Peroxycarboxylic acid (ppm) | *C. funicola* Log Reduction | *B. Cereus* Log reduction |
|---|---|---|---|---|---|
| Dimethyl Adipate | Single Phase | 0.5 | 1500 | 2.1 | 4.21 |
| Dimethyl Adipate | Single Phase | 1 | 1500 | >3.45 | 4.97 |

TABLE XVIII-continued

| Solvent type | Phases | Solvent wt-% | Peroxycarboxylic acid (ppm) | *C. funicola* Log Reduction | *B. Cereus* Log reduction |
|---|---|---|---|---|---|
| Dimethyl Suberate | Phase separation | 0.5 | 1500 | >3.45 | >6.11 |
| Dimethyl Suberate | Phase separation | 1 | 1500 | >3.45 | >6.11 |
| Diethyl Succinate | Single phase | 0.5 | 1500 | 1.8 | 4.2 |
| Diethyl Adipate | Phase separation | 0.5 | 1500 | 2.3 | >6.11 |
| DBE-3 ™ | Single phase | 1 | 1000 | 0.94 | 0.97 |
| Dimethyl Succinate | Single phase | 1 | 1000 | 0.16 | 0.23 |
| Dimethyl Glutarate | Single phase | 1 | 1000 | 0.88 | 0.59 |
| Dimethyl adipate | Single phase | 1 | 1000 | 1.02 | 1.08 |
| DBE-3 ™ | Single phase | 1 | 2000 | 3.15 | 2.29 |
| Dimethyl Succinate | Single phase | 1 | 2000 | 0.1 | 1.21 |
| Dimethyl Glutarate | Single phase | 1 | 2000 | 1.46 | 1.35 |
| Dimethyl adipate | Single phase | 1 | 2000 | 3.26 | 2.26 |
| DBE-3 ™ | Single phase | 2.5 | 1000 | >4.54 | 2.91 |
| Dimethyl Succinate | Single phase | 2.5 | 1000 | 0.54 | 0.42 |
| Dimethyl Glutarate | Single phase | 2.5 | 1000 | 1.89 | 1.53 |
| Dimethyl adipate | Single phase | 2.5 | 1000 | >4.54 | 1.46 |
| DBE-3 ™ | Single phase | 2.5 | 2000 | >4.54 | 5.76 |
| Dimethyl Succinate | Single phase | 2.5 | 2000 | 1.79 | 1.59 |
| Dimethyl Glutarate | Single phase | 2.5 | 2000 | >4.54 | 2.55 |
| Dimethyl adipate | Single phase | 2.5 | 2000 | >4.54 | 6.46 |
| DBE-3 ™ | Single phase | 1 | 1000 | 1.64 | 0.91 |
| DBE-3 ™ | Single phase | 2.5 | 1000 | >4.54 | 2.75 |
| Dimethyl Glutarate | Single phase | 1 | 1000 | 0.98 | 0.32 |
| Dimethyl Succinate | Single phase | 2.5 | 1000 | 1.02 | 0.52 |
| DBE-3 ™ | Single phase | 2 | 2000 | >4.56 | >5.58 |
| DBE-3 ™ | Single phase | 2 | 1500 | >4.56 | >5.58 |
| DBE-3 ™ | Single phase | 1.5 | 2000 | >4.56 | >5.58 |
| DBE-3 ™ | Single phase | 1.5 | 1500 | >4.56 | >5.58 |
| Dimethyl sebacate | Phase separation | 1 | 1500 | 1.12 | 5.18 |
| Dimethyl sebacate | Phase separation | 0.5 | 1500 | 1.7 | 4.7 |
| Dimethyl sebacate | Phase separation | 0.1 | 1500 | 1.38 | 4.6 |
| Dibutyl Sebacate | Phase separation | 1 | 1500 | 0.84 | 2.38 |
| Dibutyl Sebacate | Phase separation | 0.5 | 1500 | 0.26 | 2.05 |
| Dibutyl Sebacate | Phase separation | 0.1 | 1500 | 0.66 | 2.1 |
| Dioctyl Sebacate | Phase separation | 1 | 1500 | 0.98 | 0.94 |
| Dioctyl Sebacate | Phase separation | 0.5 | 1500 | 0.86 | 1.13 |
| Dioctyl Sebacate | Phase separation | 0.1 | 1500 | 0.79 | 0.99 |
| DBE-IB | Phase separation | 1 | 1500 | 0.9 | 3.24 |
| DBE-IB | Phase separation | 0.5 | 1500 | 0.93 | 3.07 |
| DBE-IB | Phase separation | 0.1 | 1500 | 0.72 | 3.18 |

This data indicates that the greatest antimicrobial activity derives from composition including a diester dicarboxylate having 5 to 8 carbon atoms in the dicarboxylate moiety and 1 to 2 carbons in the ester moiety, for a total of 6 to 10 carbon atoms in the diester dicarboxylate. Among these diester dicarboxylates, the greatest activity among diester dicarboxylates with 6 to 8 carbon atoms in the dicarboxylate moiety and 1 to 2 carbons in the ester moiety, for a total of 7 to 10 carbon atoms in the diester dicarboxylate. Among the esters exhibiting the greatest activity were methyl esters of adipic and suberic acids.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. An antimicrobial concentrate and instructions for mixing the concentrate with water;

the concentrate consisting essentially of antimicrobial solvent and antimicrobial agent;

the antimicrobial solvent being benzyl alcohol, ethylene glycol phenyl ether, propylene glycol phenyl ether, propylene carbonate, phenoxyothanol, dimethyl malonate, dimethyl succinate, diethyl succinate, dibutyl succinate, dixnethyl glutarate, diethyl glutarate, dibutyl glutarate, dimethyl adipate, diethyl adipate, dibutyl adipate, dimethyl pimelate, diethyl pimelate, dimethyl suberate, diethyl suberate, dimethyl sebacate, diethyl sebacate, or mixture thereof;

the antimicrobial agent being halogen containing antimicrobial agent, peroxycarboxylic acid, carboxylic acid, or mixture thereof;

the amounts of antimicrobial solvent and antimicrobial agent in the concentrate being sufficient so that when the concentrate is mixed with water according to the instructions the resulting mixture will provide greater than a 1-log order reduction in population of bacteria or spores of *Bacillus cereus* within 10 seconds at 60° C.

2. The concentrate of claim 1, wherein the halogen containing antimicrobial agent is hypochlorous acid, hypochlorous acid salt, chlorine dioxide, hypobromous acid, hypobromous acid salt, or interhalide.

3. The concentrate of claim 2, wherein the interhalide is iodine monochloride, iodine dichloride, iodine trichloride, iodine tetrachloride, bromine chloride, iodine monobromide, iodine dibromide, or mixture thereof.

4. The concentrate of claim 1, wherein the peroxycarboxylic acid is peroxyacetic acid, peroxyformic acid, peroxyoctanoic acid, ester peroxycarboxylic acid, salt thereof, or mixture thereof.

5. The concentrate of claim 1, wherein the carboxylic acid is aliphatic carboxylic acid, aromatic carboxylic acid, or mixture thereof.

6. The concentrate of claim 5, wherein the carboxylic acid is formic acid, acetic acid, propionic acid, heptanoic acid, octanoic acid, nonanoic acid, decanoic acid, benzoic acid, salicylic acid, salt thereof, or mixture thereof.

7. The concentrate of claim 1, wherein the antimicrobial solvent is dimethyl adipate, diethyl adipate, dibutyl adipate, dimethyl pimelate, diethyl pimelate, dimethyl suberate, diethyl suberate, dimethyl sebacate, diethyl sebacate, or mixture thereof.

8. The concentrate of claim 1, wherein the concentrate is diluted in water, glycol, $CO_2$, or mixture thereof.

9. The concentrate of claim 1, wherein when the concentrate is mixed with water according to the instructions the resulting mixture also provides greater 1-log order reduction in population of the mold *Chaetomium funicola* within 10 seconds at 60° C.

10. An antimicrobial composition consisting essentially of diluting solvent, antimicrobial solvent, and antimicrobial agent;

the diluting solvent being water, glycol, $CO_2$, or mixture thereof;

the antimicrobial solvent being benzyl alcohol, ethylene glycol phenyl ether, propylene glycol phenyl ether, propylene carbonate, phenoxyethanol, dimethyl malonate, dimethyl succinate, diethyl succinate, dibutyl succinate, dimethyl glutarate, diethyl glutarate, dibutyl glutarate, dimethyl adipate, diethyl adipate, dibutyl adipate, dimethyl pimelate, diethyl pimelate, dimethyl suberate, diethyl suberate, dimethyl sebacate, diethyl sebacate, or mixture thereof;

the antimicrobial agent being halogen containing antimicrobial agent, peroxycarboxylic acid, carboxylic acid, or mixture thereof;

wherein the antimicrobial solvent and antimicrobial agent are at concentration effective to provide greater than a 1-log order reduction in the population of bacteria or spores of *Bacillus cereus* within 10 seconds at 60° C.

11. The composition of claim 10, wherein the diluting solvent is water.

12. The composition of claim 10, wherein the halogen containing antimicrobial agent is hypochlorous acid, hypochlorous acid salt, chlorine dioxide, hypobromous acid, hypobromous acid salt, or interhalide.

13. The composition of claim 12, wherein the interhalide is iodine monochloride, iodine dichloride, iodine trichloride, iodine tetrachloride, bromine chloride, iodine monobromide, iodine dibromide, or mixture thereof.

14. The composition of claim 10, wherein the peroxycarboxylic acid is peroxyacetic acid, peroxyformic acid, peroxyoctanoic acid, ester peroxycarboxylic acid, salt thereof or mixture thereof.

15. The composition of claim 10, wherein the carboxylic acid is aliphatic carboxylic acid, aromatic carboxylic acid, or mixture thereof.

16. The composition of claim 15, wherein the carboxylic acid is formic acid, acetic acid, propionic acid, heptanoic acid, octanoic acid, nonanoic acid, decanoic acid, benzoic acid, salicylic acid, salt thereof, or mixture thereof.

17. The composition of claim 10, wherein the antimicrobial solvent is dimethyl adipate, diethyl adipate, dibutyl adipate, dimethyl pimelate, diethyl pimelate, dimethyl suberate, diethyl suberate, dimethyl sebacate, diethyl sebacate, or mixture thereof.

18. The composition of claim 10, wherein the diluting solvent is water and the antimicrobial solvent has a water solubility less than about 10% by weight.

19. The composition of claim 18, wherein the antimicrobial solvent has a water solubility less then about 5% by weight.

20. The composition of claim 19, wherein the antimicrobial solvent has a water solubility less than about 2% by weight.

21. The composition of claim 10, wherein the composition is cosolvent-free.

22. The composition of claim 10, wherein the composition is surfactant-free.

23. An antimicrobial concentrate and instructions for mixing the concentrate with water;

the concentrate consisting essentially of antimicrobial solvent, octanoic acid, hydrogen peroxide, and peroxyoctanoic acid;

the antimicrobial solvent being benzyl alcohol, ethylene glycol phenyl ether, propylene glycol phenyl ether, propylene carbonate, phenoxyethanol, dimethyl malonate, dimethyl succinate, diethyl succinate, dibutyl succinate, dimethyl glutarate, diethyl glutarate, dibutyl glutarate, dimethyl adipate, diethyl adipate, dibutyl adipate, dimethyl pimelate, diethyl pimelate, dimethyl suberate, diethyl suberate, dimethyl sebacate, diethyl sebacate, octanoic acid, or mixture thereof;

the amounts of antimicrobial solvent and peroxyoctanoic acid in the concentrate being sufficient so that when the concentrate is mixed with water according to the instructions the resulting mixture will provide greater than a 1-log order reduction in population of bacteria or spores of *Bacillus cereus* within 10 seconds at 60° C.

24. The concentrate of claim 23, wherein the antimicrobial solvent is dimethyl adipate, diethyl adipate, dibutyl adipate, dimethyl pimelate, diethyl pimelate, dimethyl suberate, diethyl suberate, dimethyl sebacate, diethyl sebacate, or mixture thereof.

25. The concentrate of claim 23, wherein the antimicrobial solvent is octanoic acid.

26. The concentrate of claim 23, wherein the concentrate is diluted in water, glycol, $CO_2$, or mixture thereof.

27. An antimicrobial composition consisting essentially of diluting solvent, antimicrobial solvent, octanoic acid, hydrogen peroxide, and peroxyoctanoic acid;

the diluting solvent being water, glycol $CO_2$, organic acid, peroxide, inorganic acid, or mixture thereof;

the antimicrobial solvent being benzyl alcohol, ethylene glycol phenyl ether, propylene glycol phenyl ether, propylene carbonate, phenoxyethanol, dimethyl malonate, dimethyl succinate, diethyl succinate, dibutyl succinate, dimethyl glutarate, diethyl glutarate, dibutyl glutarate, dimethyl adipate, diethyl adipate, dibutyl adipate, dimethyl pimelate, diethyl pimelate, dimethyl suberate, diethyl suberate, dimethyl sebacate, diethyl sebacate, octanoic acid, or mixture thereof;

wherein the antimicrobial solvent and antimicrobial agent are at concentration effective to provide greater than a 1-log order reduction in the population of bacteria or spores of *Bacillus cereus* within 10 seconds at 60° C.

28. The composition of claim 27, wherein the diluting solvent is water.

29. The composition of claim 27, wherein the antimicrobial solvent is dimethyl adipate, diethyl adipate, dibutyl adipate, dimethyl pimelate, diethyl pimelate, dimethyl suberate, diethyl suberate, dimethyl sebacate, diethyl sebacate, or mixture thereof.

30. The composition of claim 27, wherein the antimicrobial solvent is octanoic acid.

31. The composition of claim 27, wherein the diluting solvent is water and the composition has at least about 10 weight % antimicrobial solvent.

32. The composition of claim 31, having at least about 50 weight % antimicrobial solvent.

33. The composition of claim 32 having about 75 weight % to about 95 weight % antimicrobial solvent.

34. The composition of claim 27, wherein the diluting solvent is water and wherein the antimicrobial solvent is octanoic acid.

* * * * *